United States Patent [19]
Nakamura et al.

[11] Patent Number: 5,076,961
[45] Date of Patent: Dec. 31, 1991

[54] MESOMORPHIC COMPOUND, LIQUID CRYSTAL COMPOSITION CONTAINING SAME AND LIQUID CRYSTAL DEVICE USING SAME

[75] Inventors: Shinichi Nakamura, Atsugi; Takao Takiguchi, Tokyo; Takashi Iwaki, Isehara; Takeshi Togano, Yokohama; Yoko Yamada; Shosei Mori, both of Atsugi, all of Japan

[73] Assignee: Canon Kabushiki Kaisha, Tokyo, Japan

[21] Appl. No.: 549,125

[22] Filed: Jul. 6, 1990

[30] Foreign Application Priority Data

Jul. 10, 1989 [JP] Japan .................................. 1-178336

[51] Int. Cl.[5] ........................ C09K 19/34; C09K 19/52; G07D 285/12; G02F 1/13

[52] U.S. Cl. ............................. 252/299.61; 252/99.01; 548/136; 548/142; 359/103; 359/104

[58] Field of Search ....................... 252/299.01, 299.61, 252/299.62, 299.63, 299.67, 299.5; 350/350 R, 350 S; 548/136, 142

[56] References Cited

U.S. PATENT DOCUMENTS 4,952,699 8/1990 Yong et al. ......................... 548/136

FOREIGN PATENT DOCUMENTS 0335348 3/1989 European Pat. Off. .
3703651 9/1987 Fed. Rep. of Germany .
3712995 11/1988 Fed. Rep. of Germany .
3819972 1/1989 Fed. Rep. of Germany .
61472 3/1989 Japan .
2182037 5/1987 United Kingdom ........... 252/299.61
8808019 10/1988 World Int. Prop. O. ...... 252/299.01

OTHER PUBLICATIONS

Gray, G. W. et al., "Liquid Crystals & Plastic Crystals", vol. 1, John Wiley & Sons, Inc., N.Y., pp. 142-143 (1974).
Dimitrowa, K. et al., J. Prakt, Chemie, vol. 322, No. 6, pp. 933-944 (1980).
N. Herdegger, Helvetica Chimica Acta., vol. 39 (1956) 505:13.
N. Herdegger, Helvetica Chimica Acta., vol. 40 (1957) 2428:33.
R. Tschesche, Chem. Ber., vol. III (1978) 3502:05.
The Merck Index, Tenth Edition (1983) 4190.
E. F. Gramsbergen, Physics Letters, vol. 97A, No. 5 (1983) 199-201.
D. Demus et al., Flussige Kristalle in Tabellen II (1984) 359:60.
P. B. Rasmussen et al., Bull. Soc. Chim. Fr., No. 1 (1985) 62:65.

*Primary Examiner*—Robert L. Stoll
*Assistant Examiner*—Shean C. Wu
*Attorney, Agent, or Firm*—Fitzpatrick, Cella, Harper & Scinto

[57] ABSTRACT

A mesomorphic compound represented by the following formula (I):

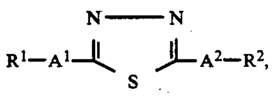

(I)

wherein $R^1$ and $R^2$ respectively denote a linear or branched alkyl group having 1-18 carbon atoms capable of including one or two or more non-neighboring methylene groups which can be replaced with at least one species of —Z—,

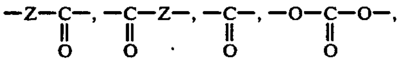

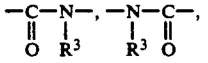

—CH=CH— and —C≡C—, wherein Z denotes —O— or —S— and $R^3$ denotes hydrogen or an alkyl group having 1-5 carbon atoms; $A^1$ denotes (Abstract continued on next page.)

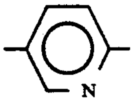 or 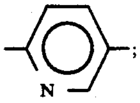;
and $A^2$ denotes any one of
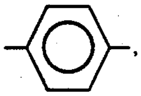, 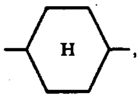, 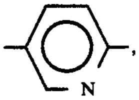,
-continued
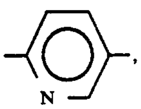, 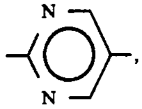, 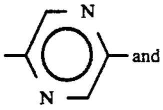 and
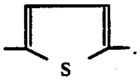.
The mesomorphic compound is effective for providing a ferroelectric liquid crystal composition showing an improved low-temperature operation characteristic and a decreased temperature-dependence of response speed.
136 Claims, 2 Drawing Sheets

MESOMORPHIC COMPOUND, LIQUID CRYSTAL COMPOSITION CONTAINING SAME AND LIQUID CRYSTAL DEVICE USING SAME

FIELD OF THE INVENTION AND RELATED ART

The present invention relates to a novel mesomorphic compound, a liquid crystal composition containing the compound and liquid crystal device using the composition, and more particularly to a novel liquid crystal composition with improved responsiveness to an electric field and a liquid crystal device using the liquid crystal composition for use in a liquid crystal display apparatus, a liquid crystal-optical shutter, etc.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 5, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4367924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic high-speed responsiveness, etc. Among a response time $\tau$, the magnitude of spontaneous polarization Ps and viscosity $\eta$, the following relationship exists: $\tau=\eta/(Ps\cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°–40° C., the response speed changes by a factor of about 20, so that it actually exceeds the range controllable by driving voltage and frequency.

As described hereinabove, commercialization of a ferroelectric liquid crystal device requires a ferroelectric chiral smectic liquid crystal composition having a low viscosity, a high-speed responsiveness and a small temperature-dependence of response speed.

SUMMARY OF THE INVENTION

An object of the present invention is to provide a mesomorphic compound, a liquid crystal composition, particularly a ferroelectric chiral smectic liquid crystal composition, containing the mesomorphic compound for providing a practical ferroelectric liquid crystal device, and a liquid crystal device using the liquid crystal composition and having a high response speed and a smaller temperature-dependence of the response speed.

According to the present invention, there is provided a mesomorphic compound represented by the following formula (I):

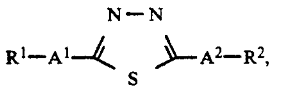 (I)

wherein $R^1$ and $R^2$ respectively denote a linear or branched alkyl group having 1-18 carbon atoms capable of including one or non-neighboring two or more methylene groups which can be replaced with at least one species of —Z—,

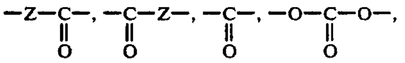

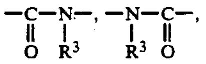

—CH=CH— and —C≡C—, wherein Z denotes —O— or —S— and $R^3$ denotes hydrogen or an alkyl group having 1-5 carbon atoms; $A^1$ denotes

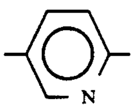 or 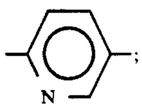;

and $A^2$ denotes any one of

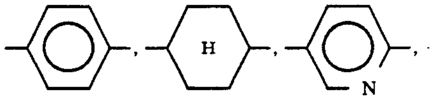

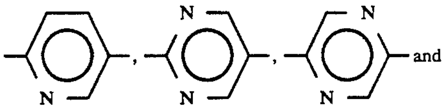 and

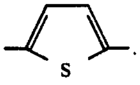.

According to the present invention, there is further provided a ferroelectric chiral smectic liquid crystal composition containing at least one species of the mesomorphic compound as described above.

The present invention further provides a liquid crystal device comprising a pair of substrates and such a ferroelectric liquid crystal composition as described above disposed between the electrode plates.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
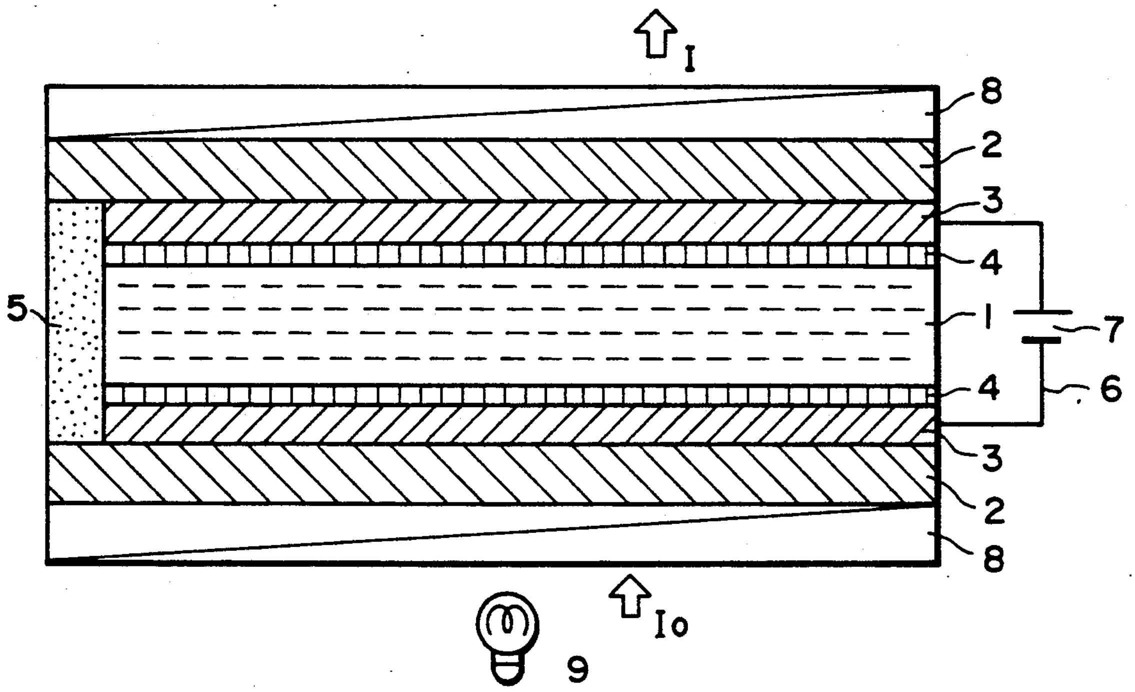
FIG. 1 is a schematic sectional view of a liquid crystal display device using a ferroelectric liquid crystal.

In the formula (I) as described above, preferred examples of $R_1$ and $R_2$ may respectively include the following groups (i) to (iii):

(i) n-alkyl group having 1-18 carbon atoms, particularly having 4-14 carbon atoms;

(ii)

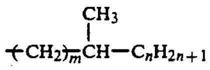

wherein m is 1-7 and n is 2-9 (optically active or inactive); and (iii)

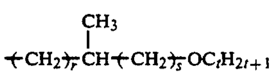

wherein r is 0-7, s is 0 or 1 and t is 1-14 (optically active or inactive).

Heretofore, liquid crystals containing a thiadiazole ring have been shown in D. Demus, H. Zaschke, "Flüssige Kristalle in Tabellen II", 1984 (VEB Deutscher Verlag Für Grundstoffindustrie). However, all of them are only those containing a thiadiazole ring and a benzene ring or cyclohexane ring. Accordingly, liquid crystals containing a thiadiazole ring and a pyridine ring are not shown or suggested at all.

The mesomorphic compounds represented by the general formula (I) may be synthesized through the following reaction schemes.

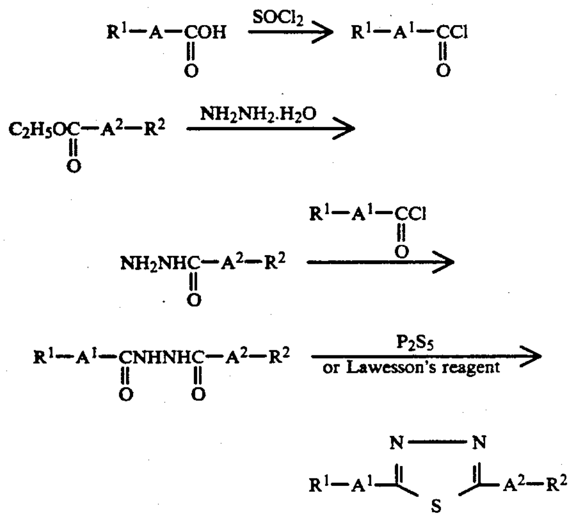

In the above, $R^1$, $R^2$, $A^1$ and $A^2$ are the same as defined in the general formula (I).

Pyridinecarboxylic acids

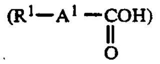

as raw materials can be synthesized by using methods shown in Hardegger, Nikles, "Helv. Chim. Act", 39, 505 (1956), 40, 2428 (1957); R. Tschesche, W. Führer, "Ber.", 111, 3502 (1978); Japanese Laid-Open Patent Application (KOKAI) No. 45258/1988, etc.

Further, ring-closing reaction using Lawesson's reagent can be conducted by using methods shown in P. B. Rasmussen et al., "Bull. Soc. Chim. Fr." No. 1, 62–65 (1985), etc.

In a case where a methylene group in $R^1$ or $R^2$ adjacent to $A^1$ or $A^2$ is replaced with —Z—,

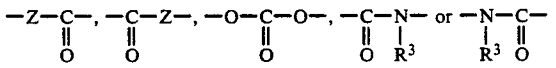

wherein Z denotes —O— or —S— and $R^3$ denotes hydrogen or an alkyl group having 1–5 carbon atoms, it is possible to form a group of $R^1$—$A^1$— or $R^2$—$A^2$— through the following steps (a) to (c):

(a) The above-mentioned replacing group combined with $A^1$ or $A^2$ is modified with addition of a protective group into a non-reactive or less reactive group such as —$OCH_3$,

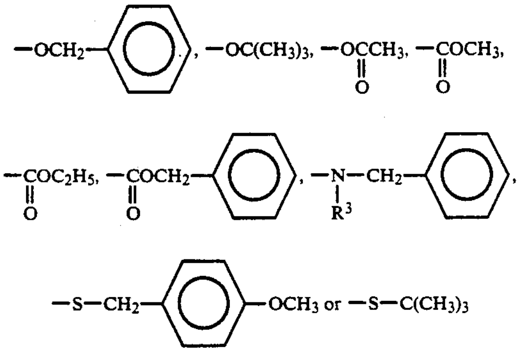

capable of elimination reaction.

(b) Ring closure is effected to form a thiadiazole ring.

(c) The protective group is eliminated and then the $R^1$—$A^1$— or $R^2$—$A^2$— structure is formed.

Specific examples of the mesomorphic compounds represented by the above-mentioned general formula (I) may include those shown by the following structural formulas.

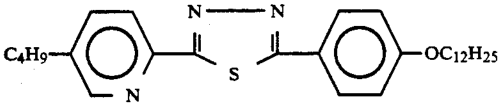
(1-1)

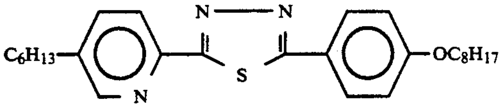
(1-2)

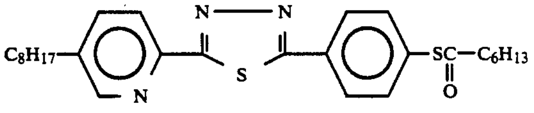
(1-3)

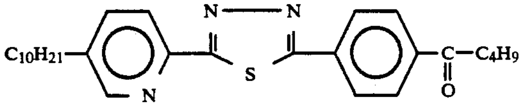
(1-4)

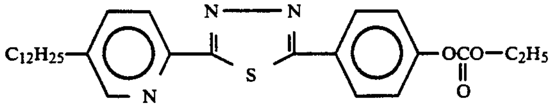
(1-5)

-continued
(1-6)
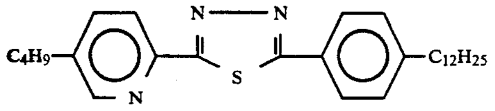
(1-7)
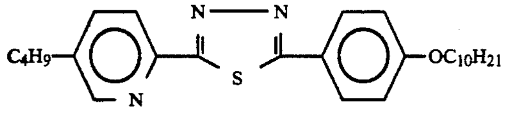
(1-8)
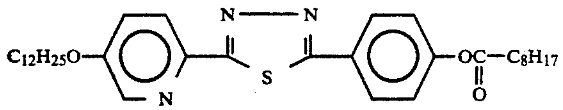
(1-9)
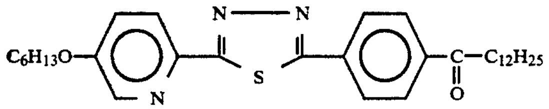
(1-10)
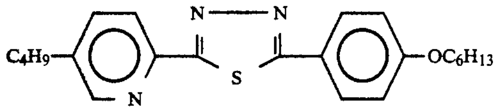
(1-11)
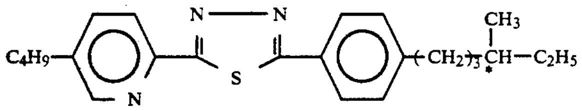
(1-12)
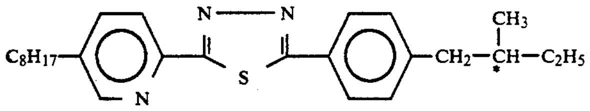
(1-13)
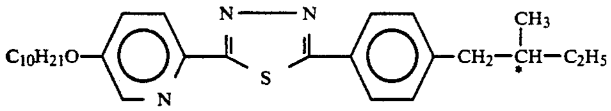
(1-14)
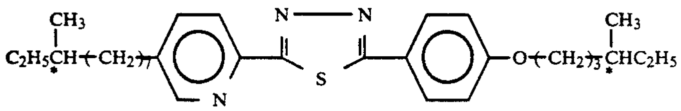
(1-15)
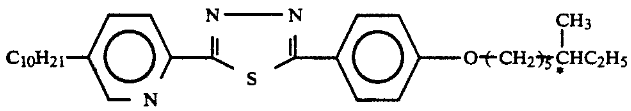
(1-16)
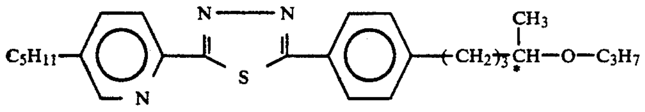
(1-17)
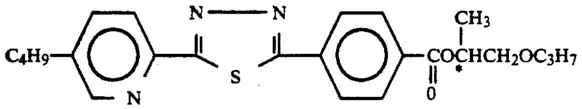
(1-18)
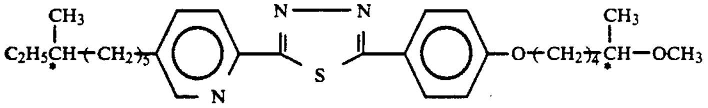

-continued
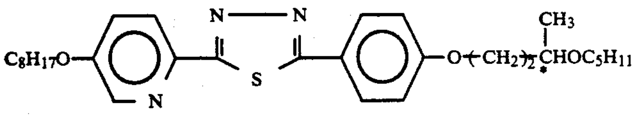
(1-19)
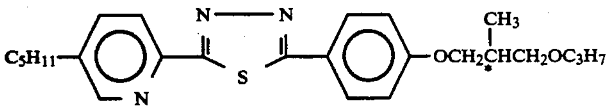
(1-20)
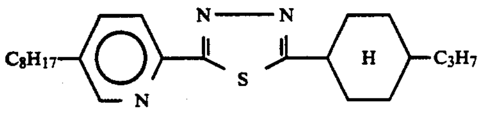
(1-21)
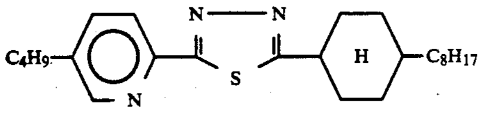
(1-22)
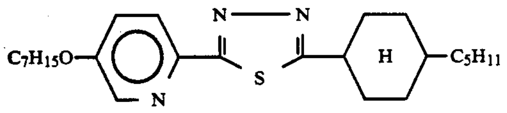
(1-23)
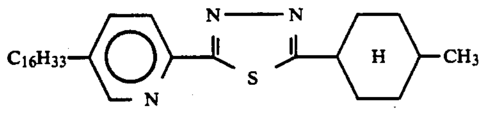
(1-24)
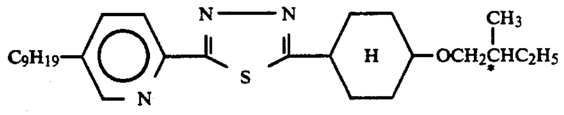
(1-25)
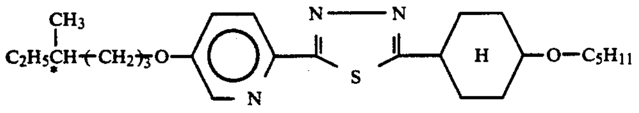
(1-26)
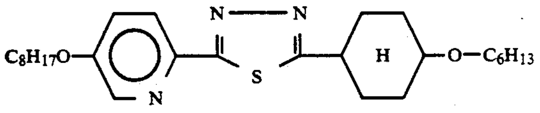
(1-27)
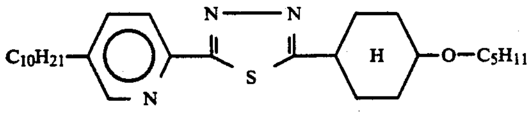
(1-28)
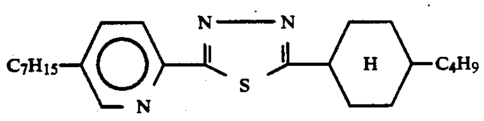
(1-29)
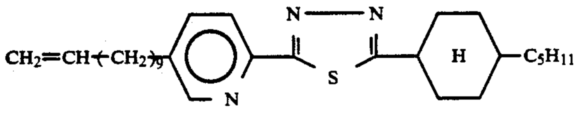
(1-30)
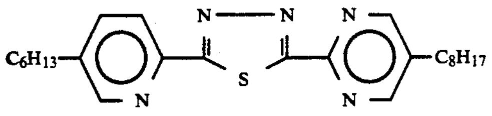
(1-31)

-continued
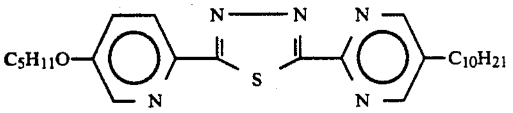
(1-32)
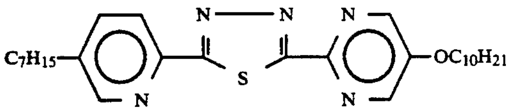
(1-33)
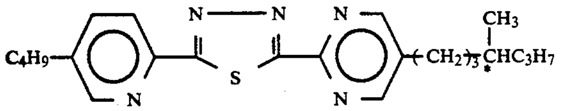
(1-34)
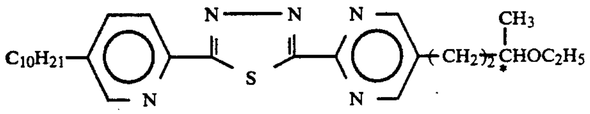
(1-35)
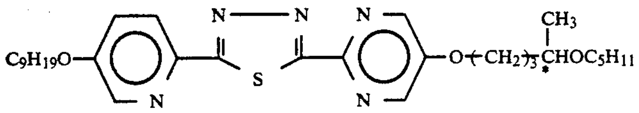
(1-36)
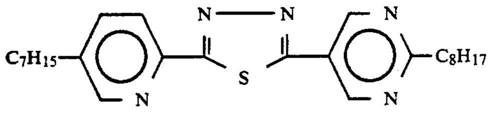
(1-37)
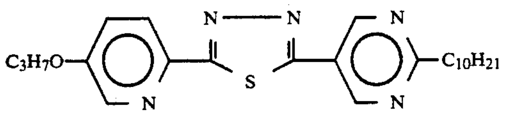
(1-38)
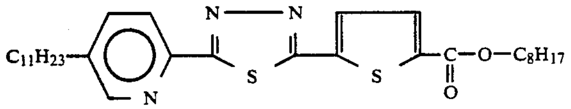
(1-39)
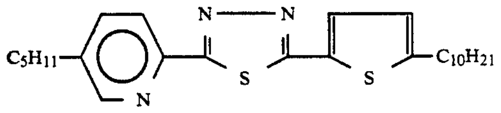
(1-40)
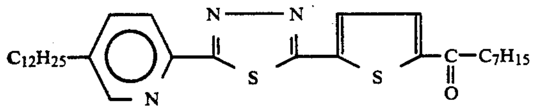
(1-41)
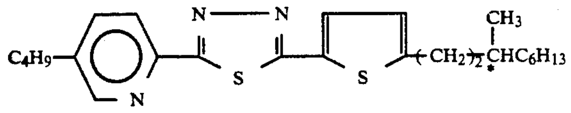
(1-42)
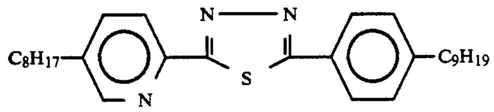
(1-43)
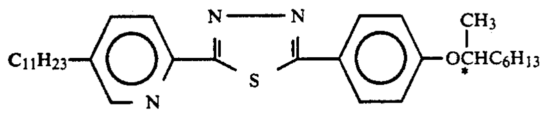
(1-44)

-continued
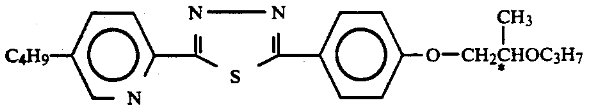
(1-45)
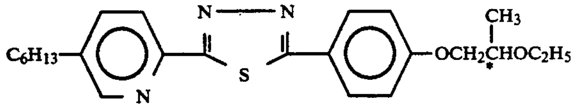
(1-46)
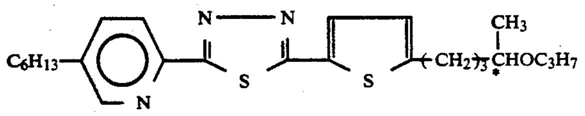
(1-47)
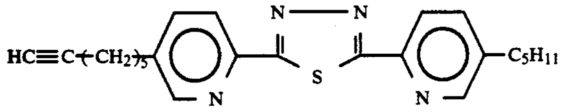
(1-48)
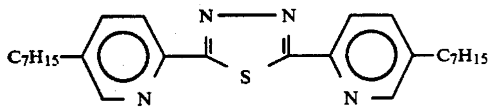
(1-49)
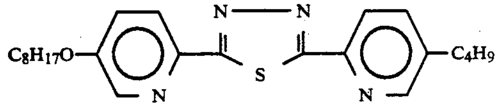
(1-50)
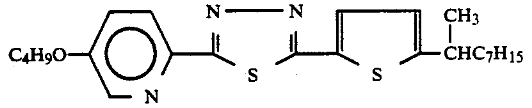
(1-51)
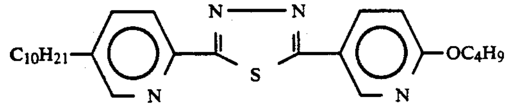
(1-52)
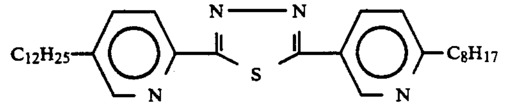
(1-53)
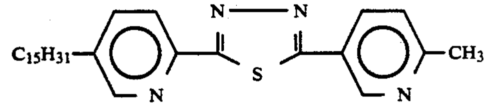
(1-54)
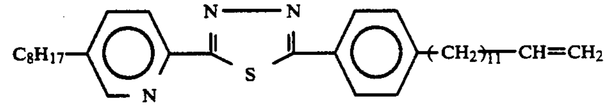
(1-55)
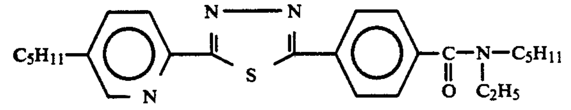
(1-56)
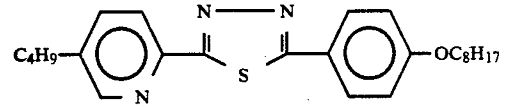
(1-57)

-continued
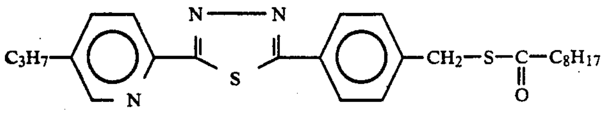
(1-58)
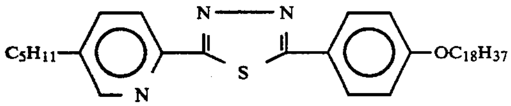
(1-59)
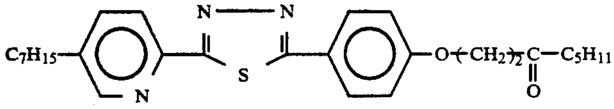
(1-60)
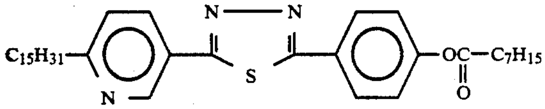
(1-61)
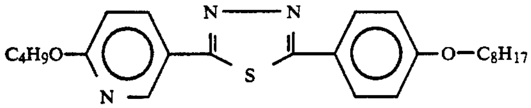
(1-62)
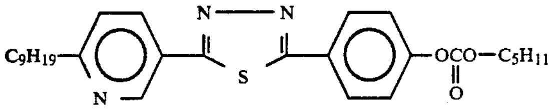
(1-63)
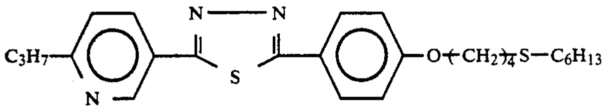
(1-64)
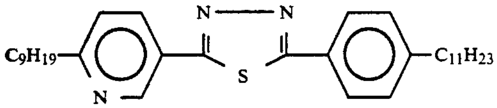
(1-65)
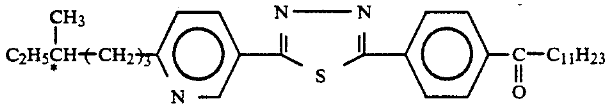
(1-66)
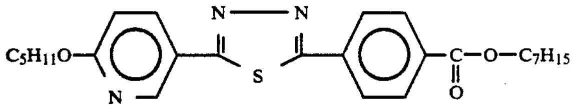
(1-67)
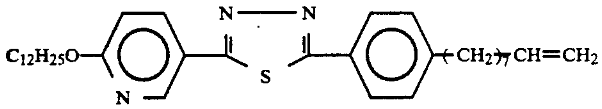
(1-68)
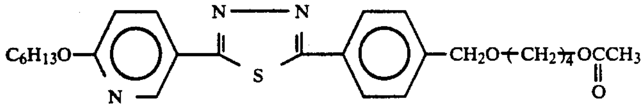
(1-69)
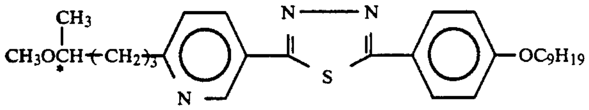
(1-70)

-continued
(1-71)
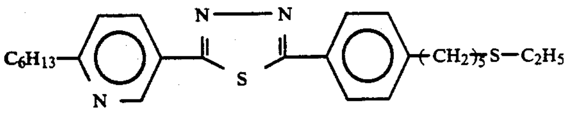
(1-72)
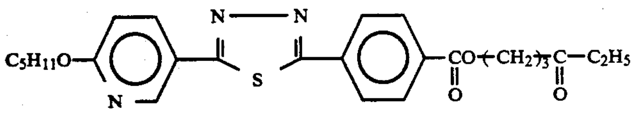
(1-73)
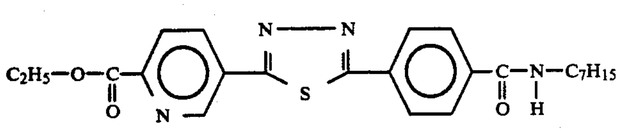
(1-74)
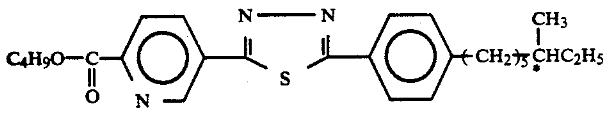
(1-75)
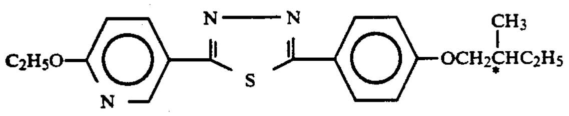
(1-76)
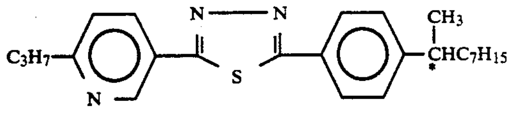
(1-77)
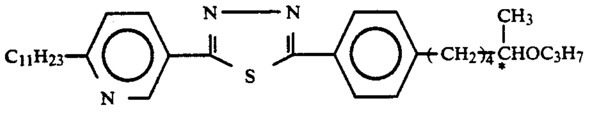
(1-78)
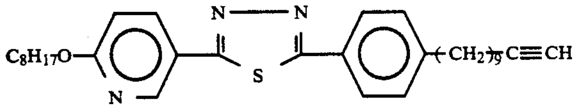
(1-79)
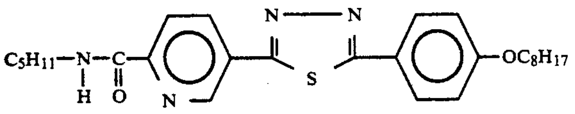
(1-80)
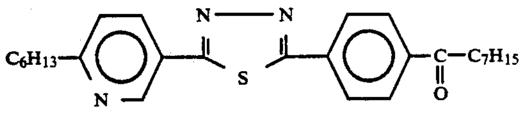
(1-81)
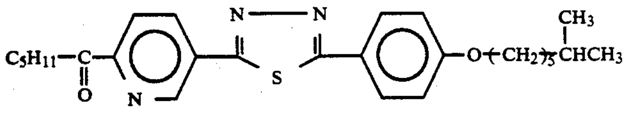
(1-82)
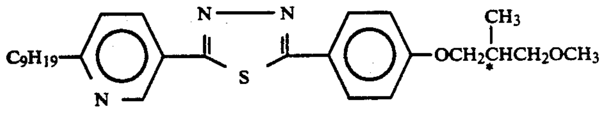
(1-83)
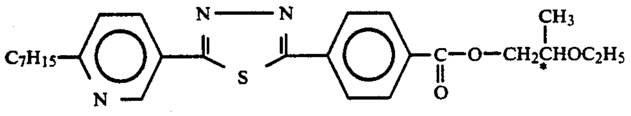

-continued
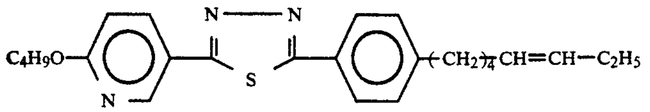
(1-84)
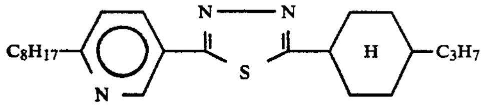
(1-85)
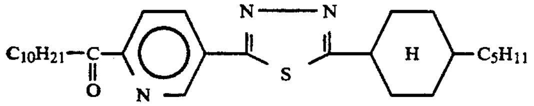
(1-86)
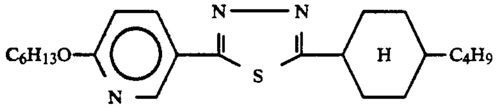
(1-87)
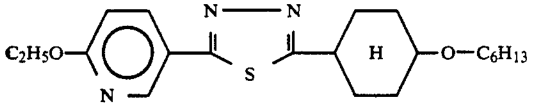
(1-88)
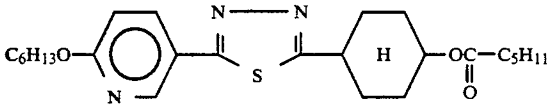
(1-89)
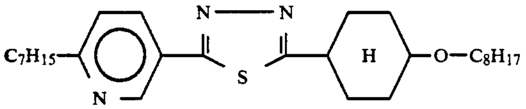
(1-90)
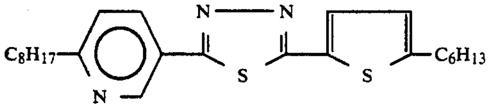
(1-91)
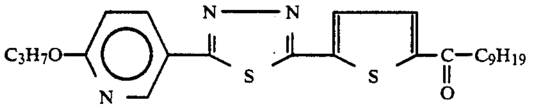
(1-92)
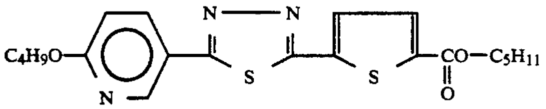
(1-93)
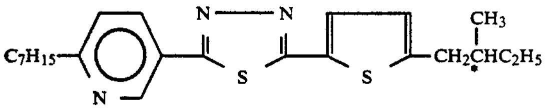
(1-94)
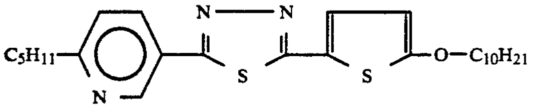
(1-95)
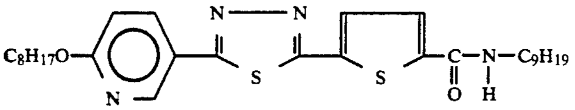
(1-96)

-continued
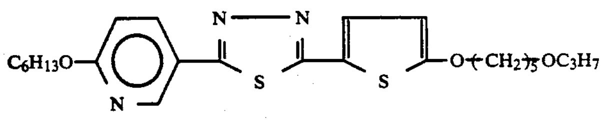
(1-97)
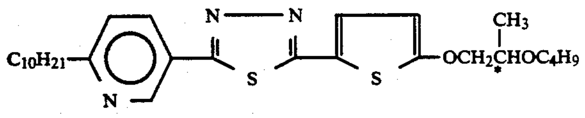
(1-98)
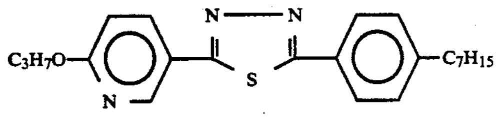
(1-99)
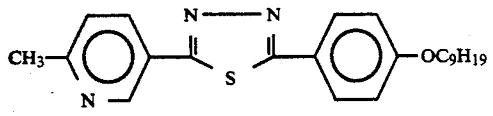
(1-100)
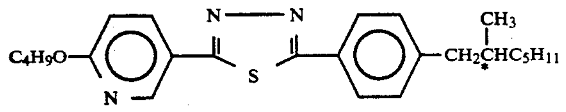
(1-101)
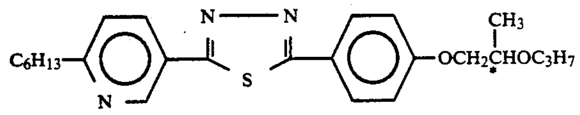
(1-102)
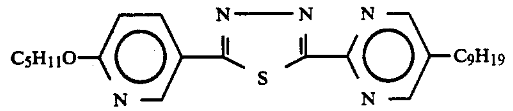
(1-103)
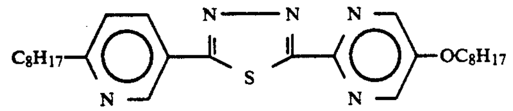
(1-104)
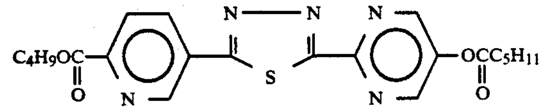
(1-105)
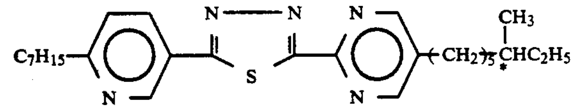
(1-106)
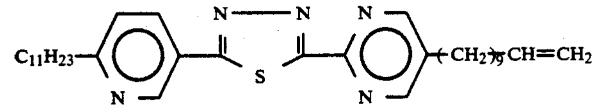
(1-107)
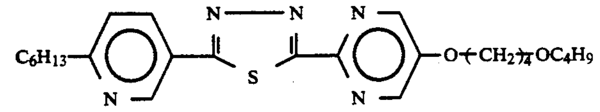
(1-108)
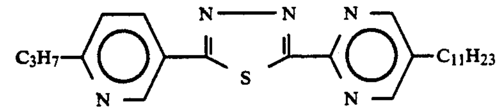
(1-109)

-continued
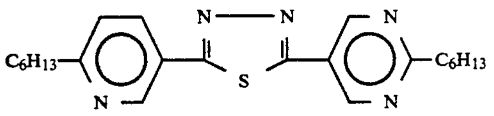
(1-110)
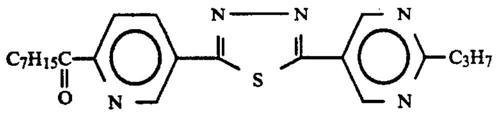
(1-111)
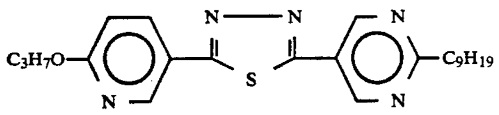
(1-112)
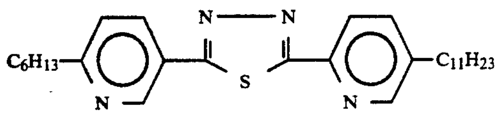
(1-113)
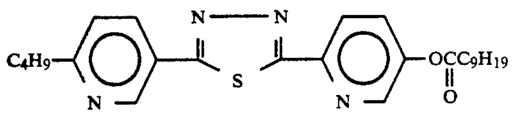
(1-114)
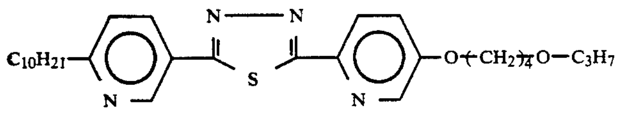
(1-115)
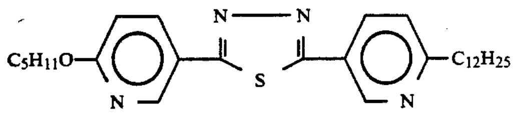
(1-116)
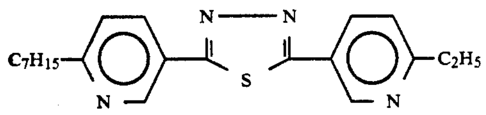
(1-117)
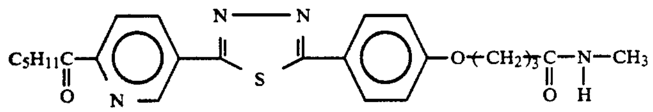
(1-118)
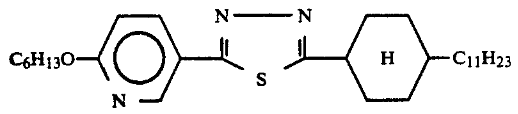
(1-119)
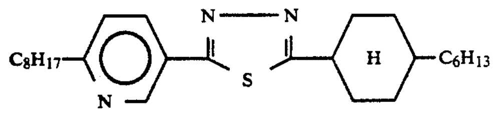
(1-120)
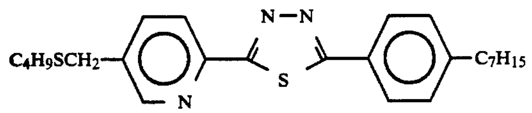
(1-121)
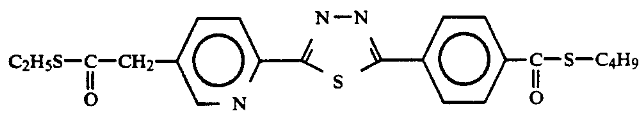
(1-122)

-continued

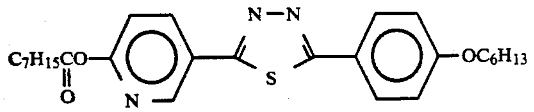

(1-123)

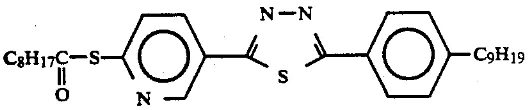

(1-124)

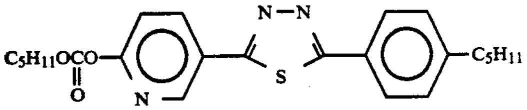

(1-125)

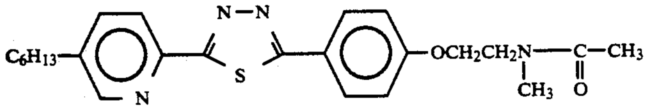

(1-126)

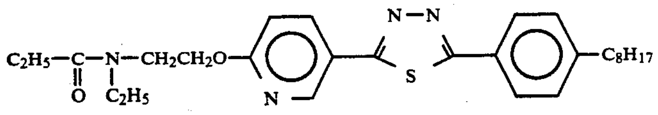

(1-127)

The liquid crystal composition according to the present invention may be obtained by mixing at least one species of the compound represented by the formula (I) and another mesomorphic compound in appropriate proportions. The liquid crystal composition according to the present invention may preferably be formulated as a ferroelectric liquid crystal composition, particularly a ferroelectric chiral smectic liquid crystal composition.

Specific examples of another mesomorphic compound as described above may include those denoted by the following structural formulas.

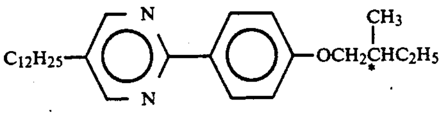

(1)

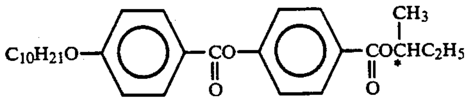

(2)

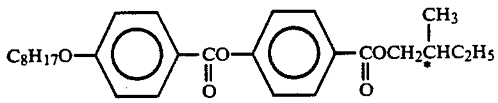

(3)

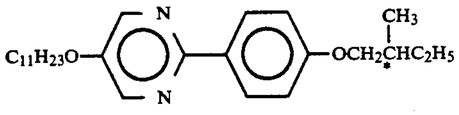

(4)

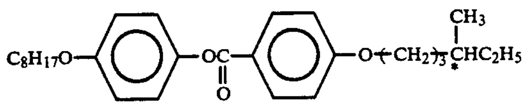

(5)

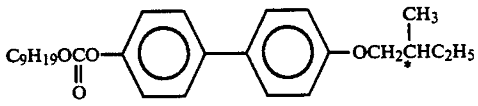

(6)

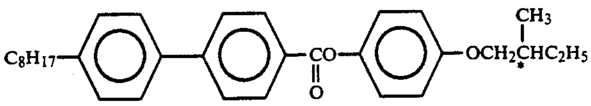

(7)

-continued
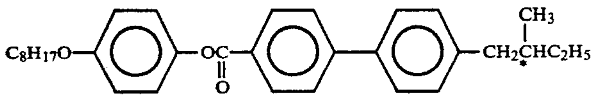
(8)
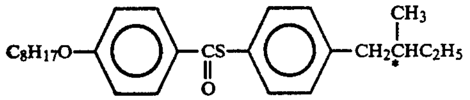
(9)
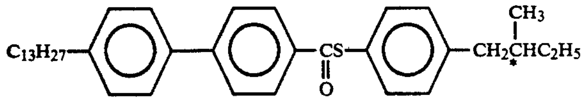
(10)
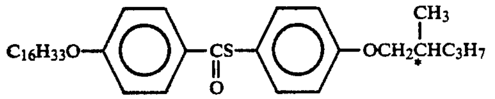
(11)
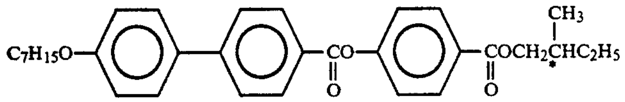
(12)
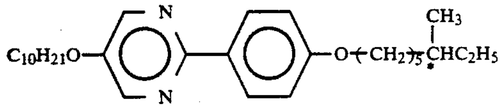
(13)
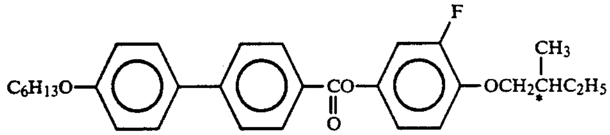
(14)
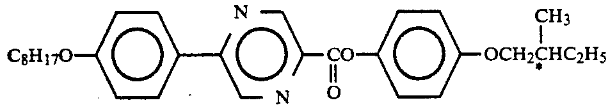
(15)
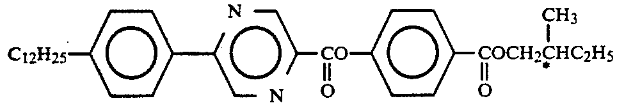
(16)
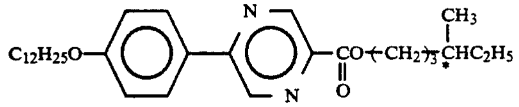
(17)
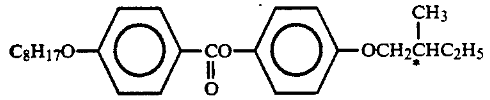
(18)
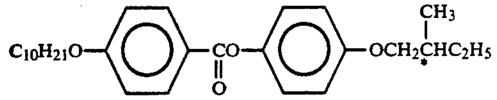
(19)
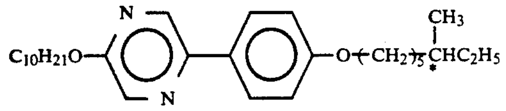
(20)

-continued
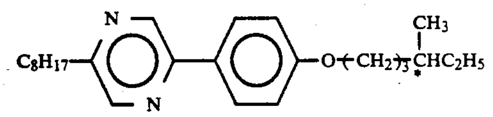
(21)
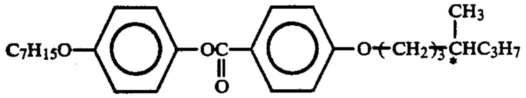
(22)
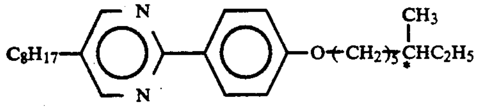
(23)
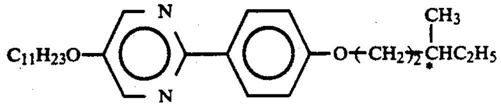
(24)
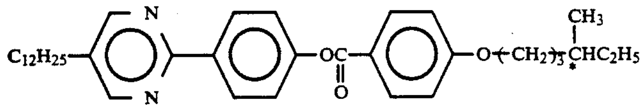
(25)
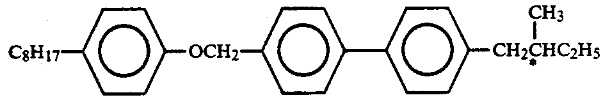
(26)
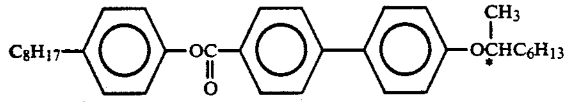
(27)
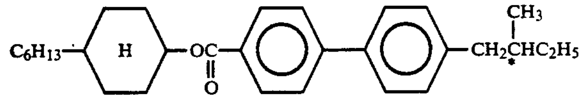
(28)
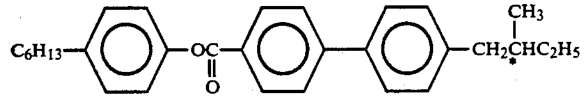
(29)
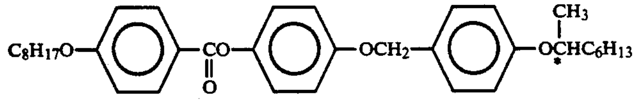
(30)
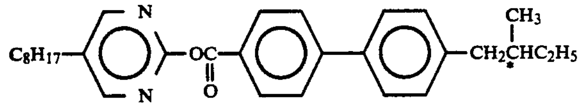
(31)
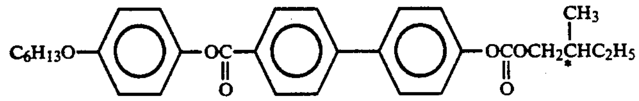
(32)
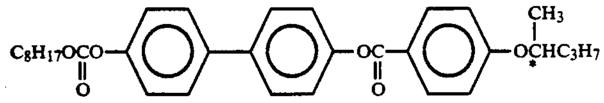
(33)

-continued
(34)
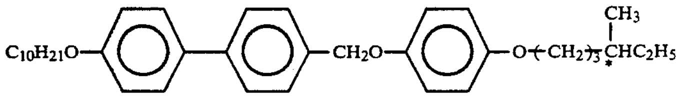
(35)
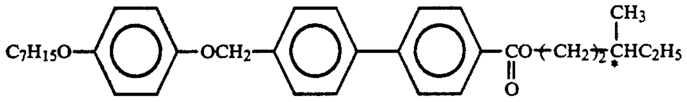
(36)
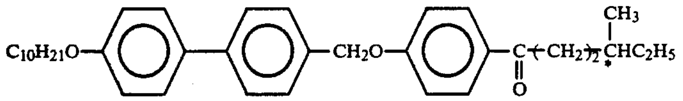
(37)
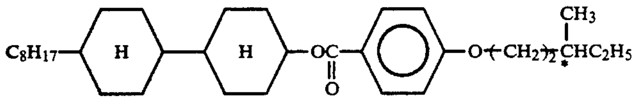
(38)
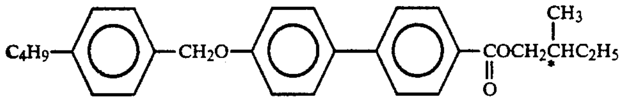
(39)
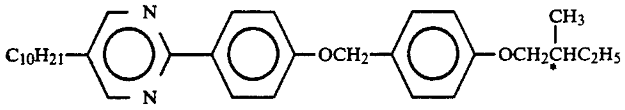
(40)
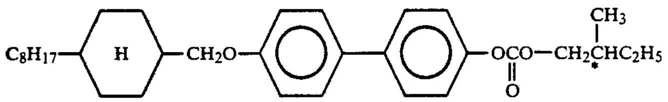
(41)
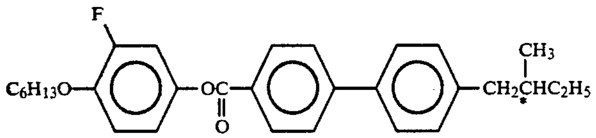
(42)
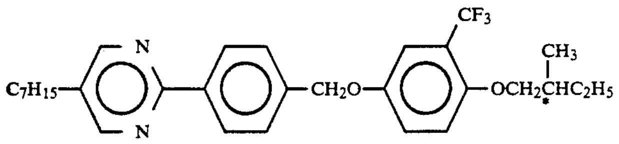
(43)
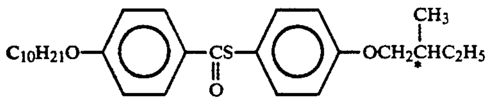
(44)
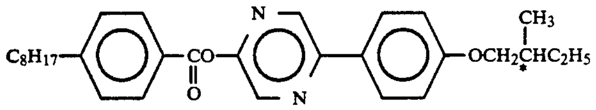
(45)
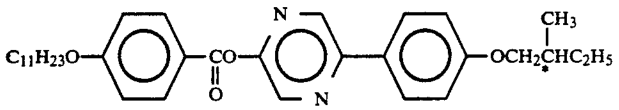
(46)
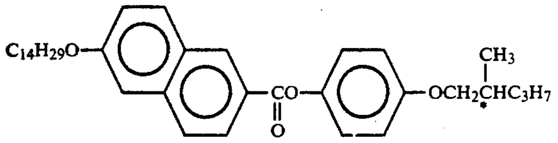

-continued
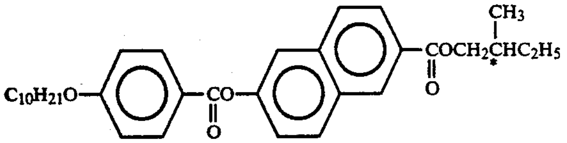
(47)
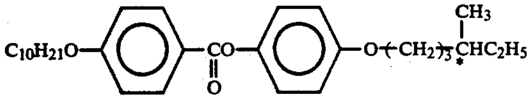
(48)
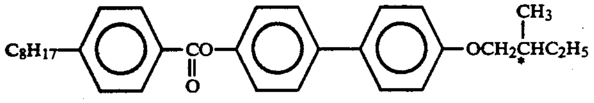
(49)
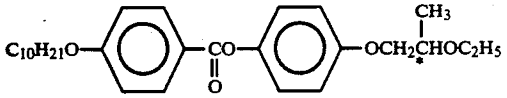
(50)
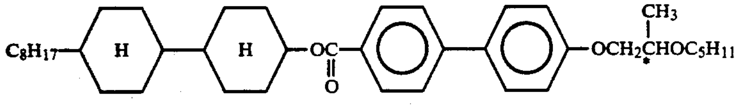
(51)
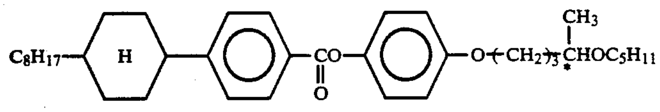
(52)
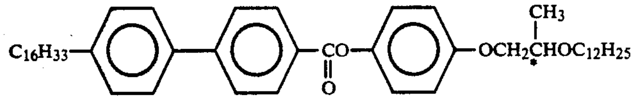
(53)
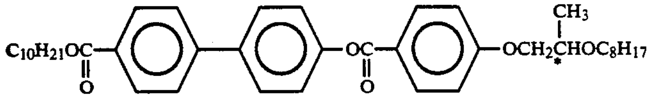
(54)
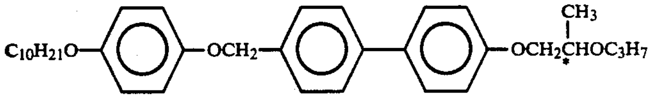
(55)
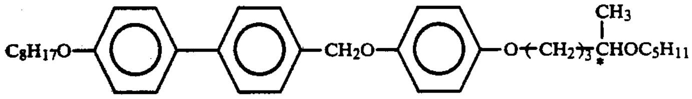
(56)
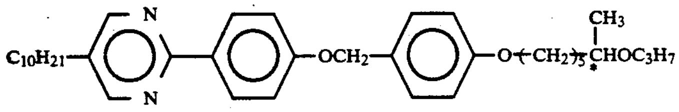
(57)
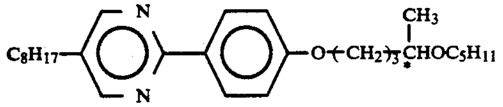
(58)
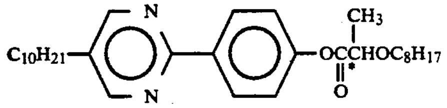
(59)

-continued
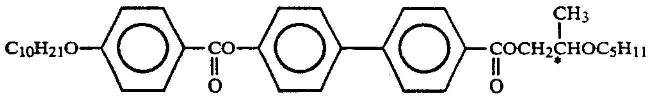
(60)
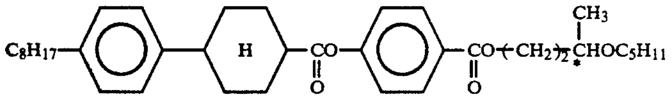
(61)
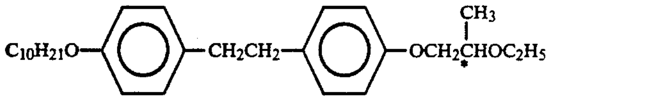
(62)
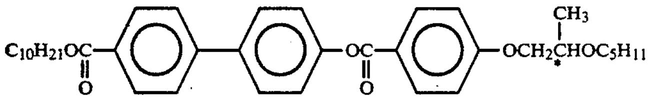
(63)
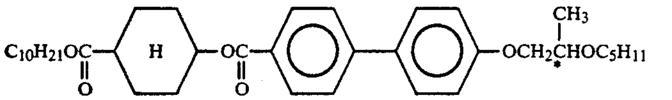
(64)
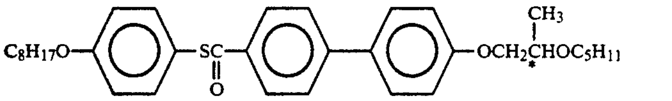
(65)
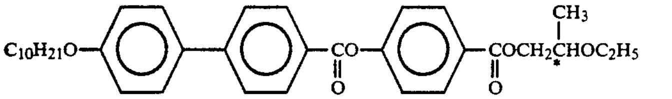
(66)
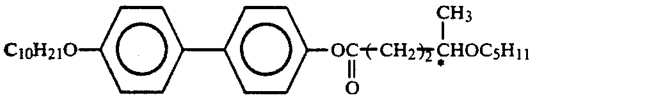
(67)
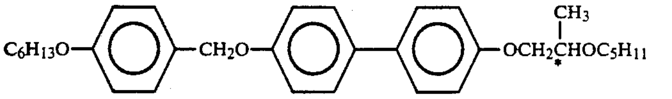
(68)
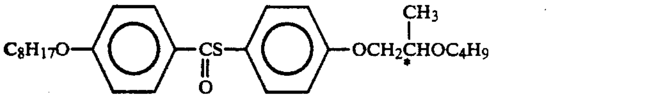
(69)
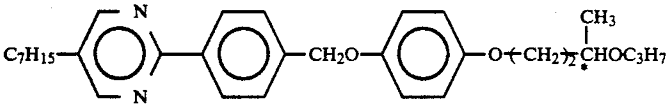
(70)
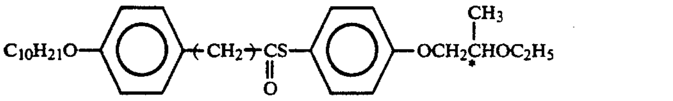
(71)
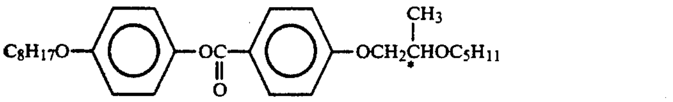
(72)

-continued
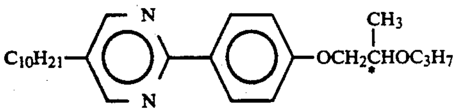
(73)
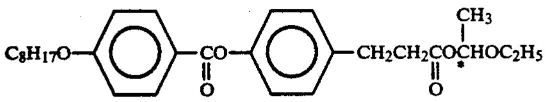
(74)
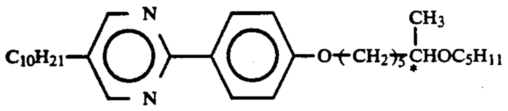
(75)
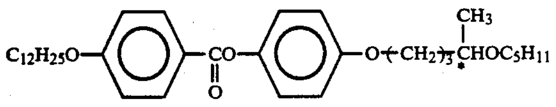
(76)
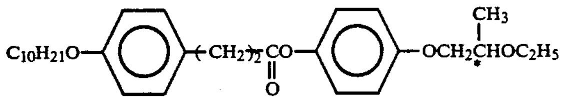
(77)
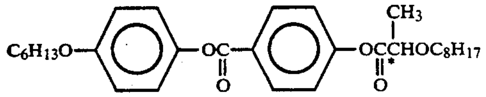
(78)
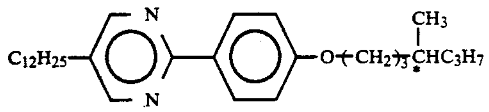
(79)
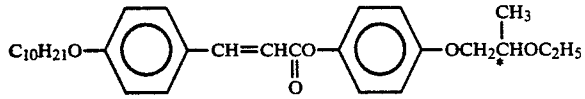
(80)
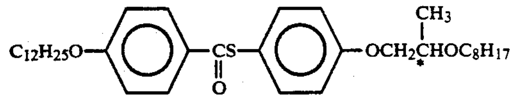
(81)
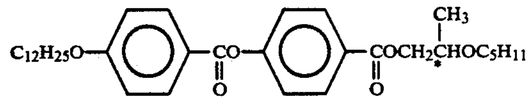
(82)
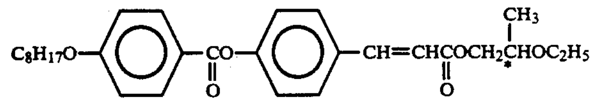
(83)
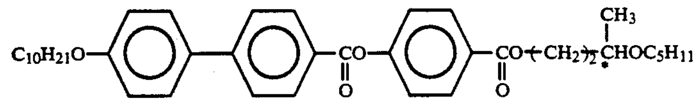
(84)
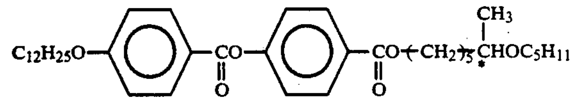
(85)

-continued
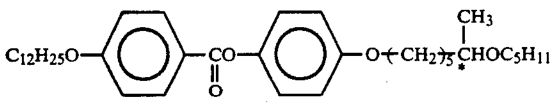
(86)
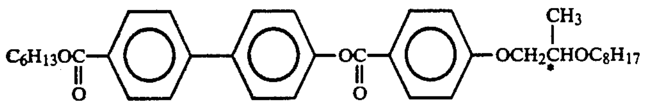
(87)
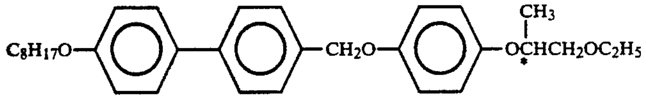
(88)
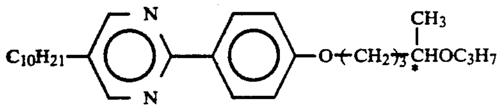
(89)
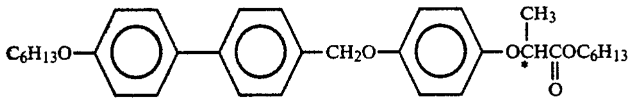
(90)
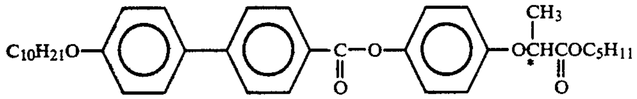
(91)
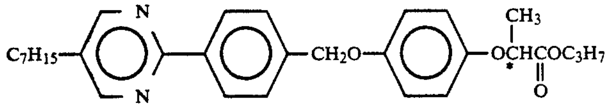
(92)
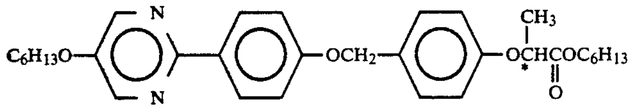
(93)
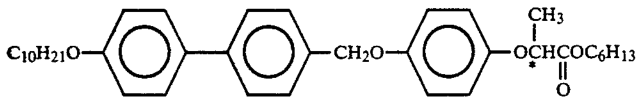
(94)
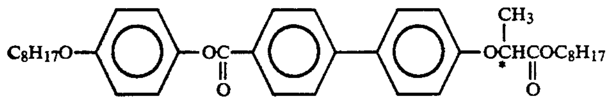
(95)
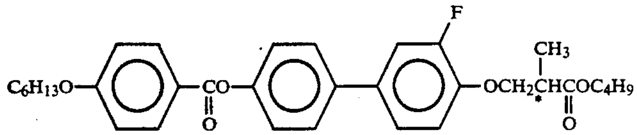
(96)
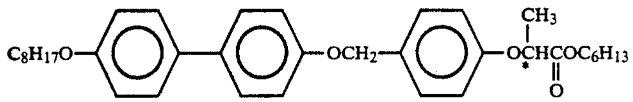
(97)
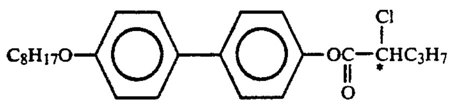
(98)

-continued
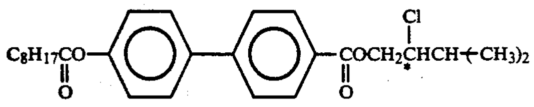
(99)
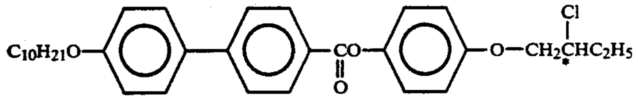
(100)
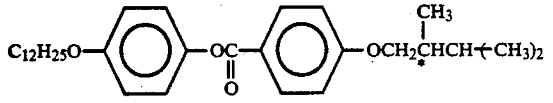
(101)
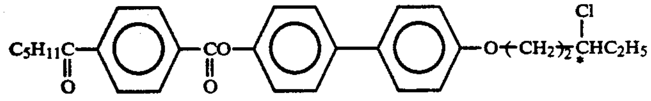
(102)
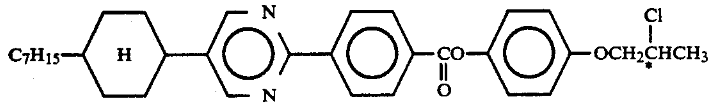
(103)
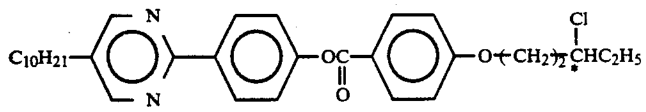
(104)
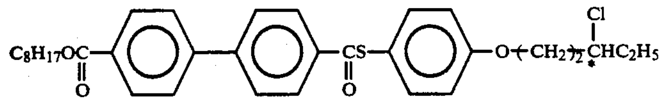
(105)
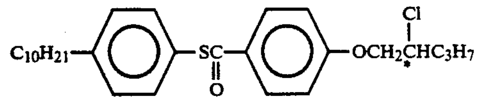
(106)
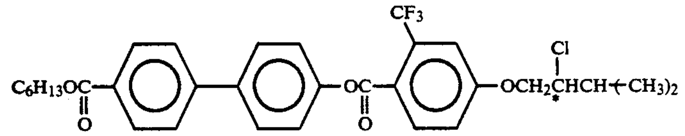
(107)
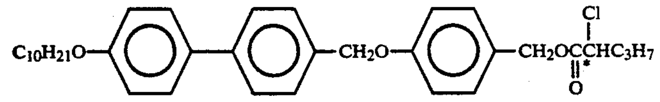
(108)
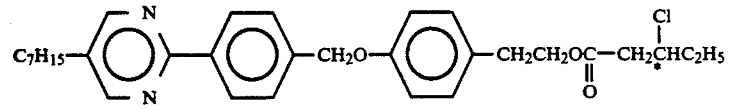
(109)
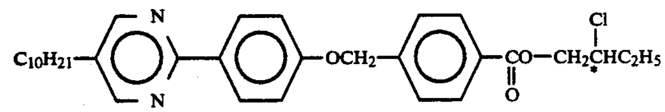
(110)
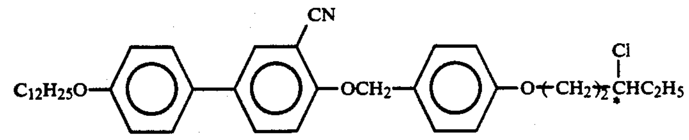
(111)

-continued
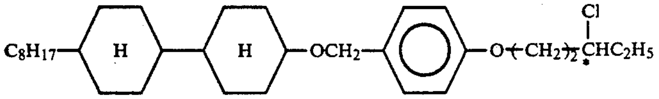
(112)
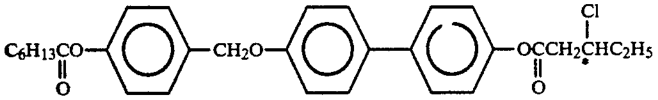
(113)
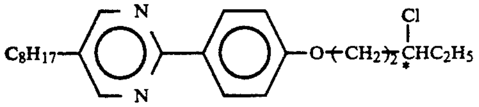
(114)
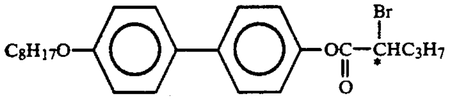
(115)
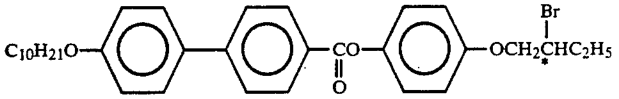
(116)
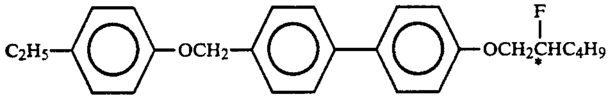
(117)
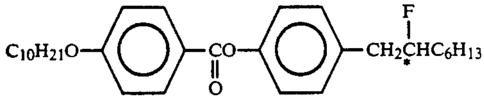
(118)
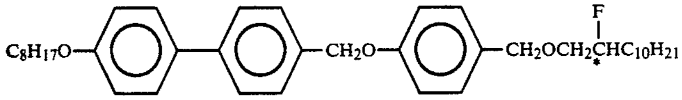
(119)
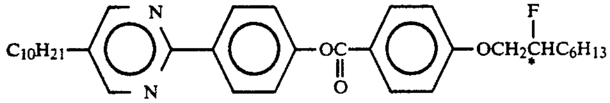
(120)
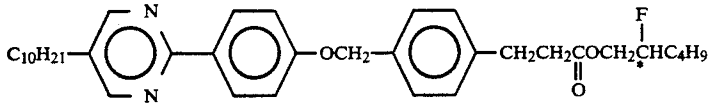
(121)
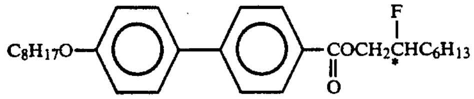
(122)
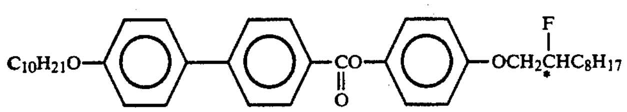
(123)
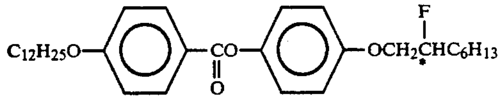
(124)

-continued
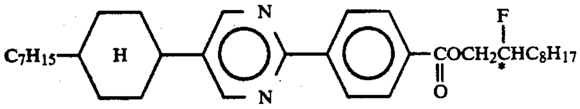
(125)
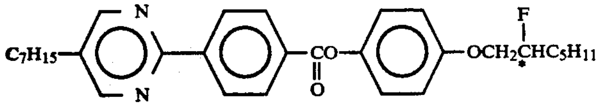
(126)
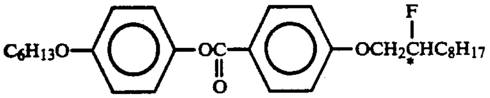
(127)
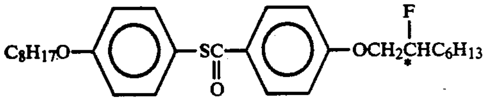
(128)
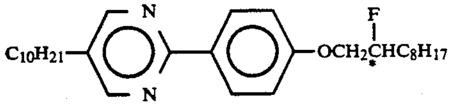
(129)
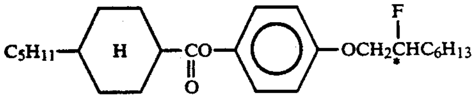
(130)
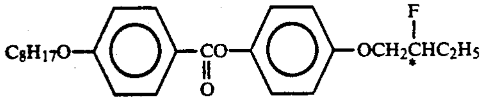
(131)
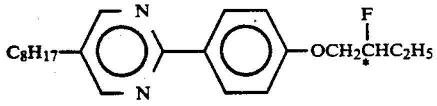
(132)
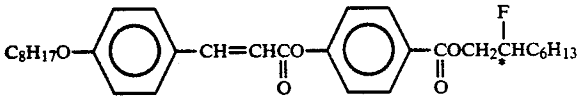
(133)
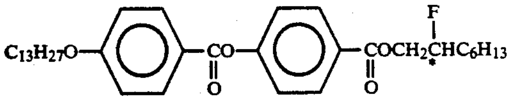
(134)
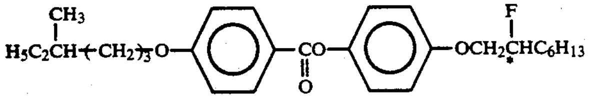
(135)
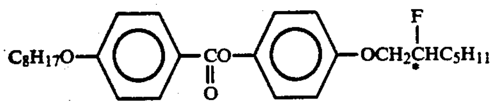
(136)
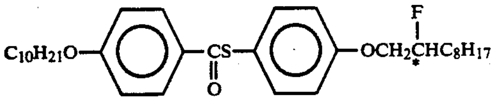
(137)

-continued
(138)
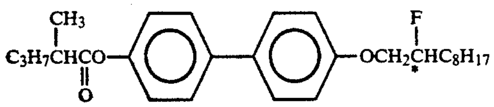
(139)
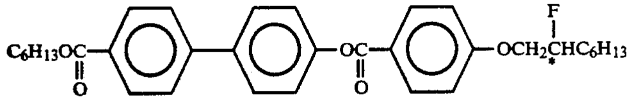
(140)
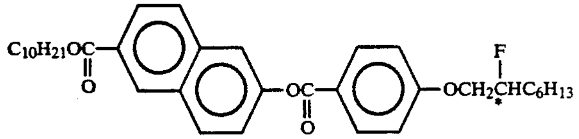
(141)
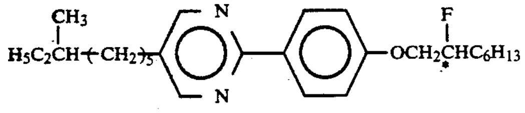
(142)
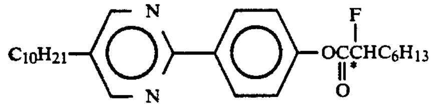
(143)
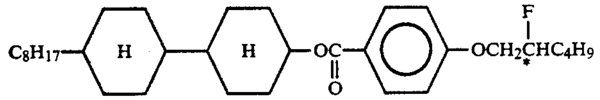
(144)
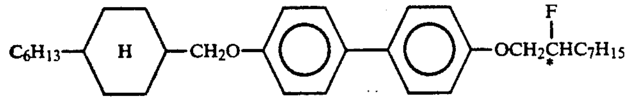
(145)
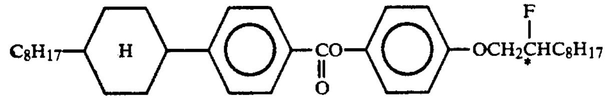
(146)
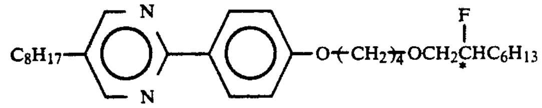
(147)
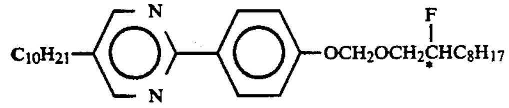
(148)
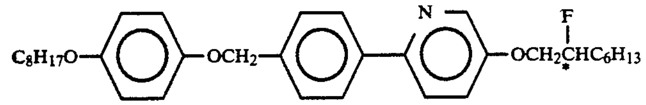
(149)
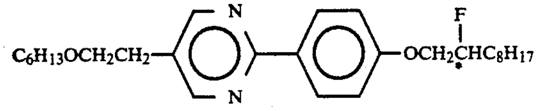
(150)
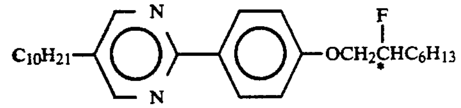

-continued
(151)
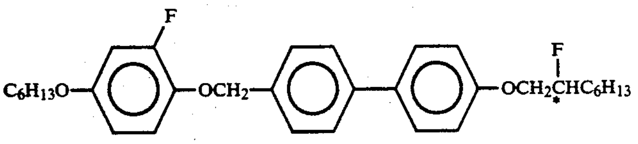
(152)
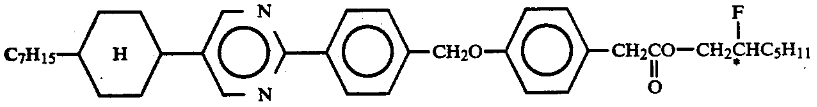
(153)
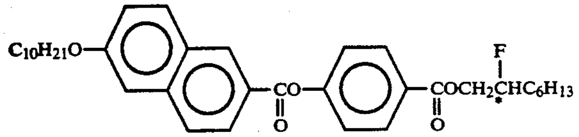
(154)
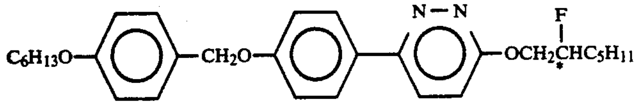
(155)
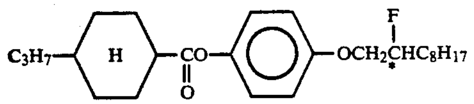
(156)
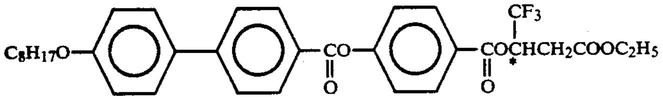
(157)
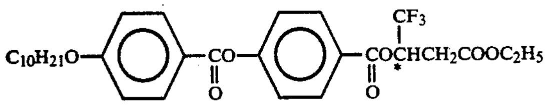
(158)
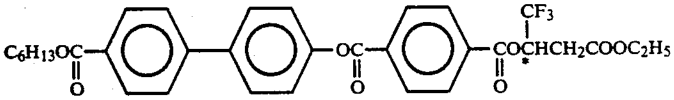
(159)
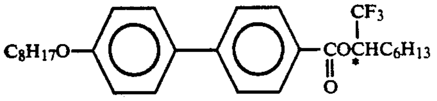
(160)
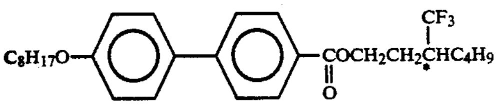
(161)
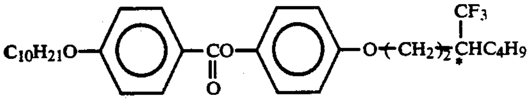
(162)
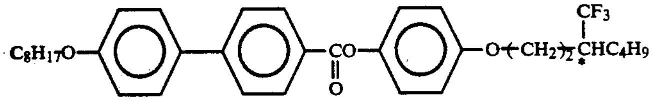
(163)
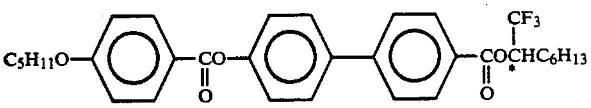

-continued
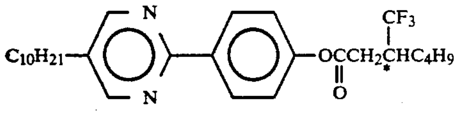
(164)
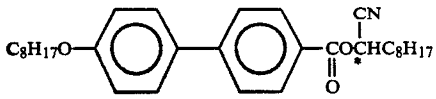
(165)
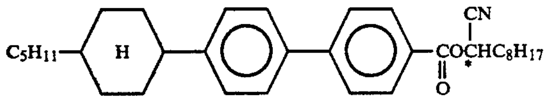
(166)
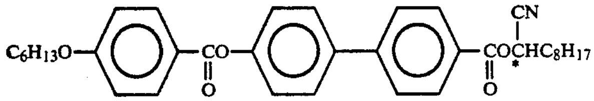
(167)
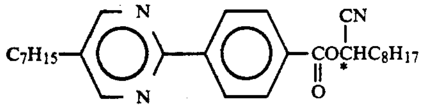
(168)
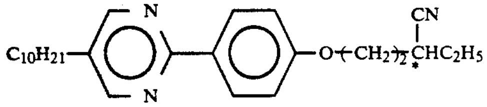
(169)
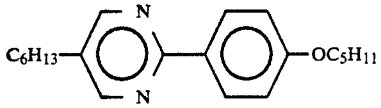
(170)
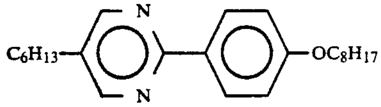
(171)
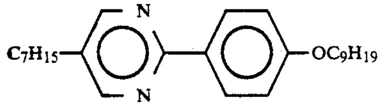
(172)
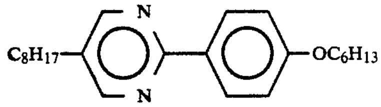
(173)
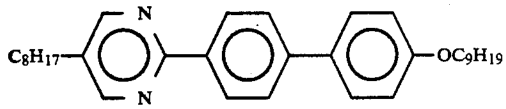
(174)
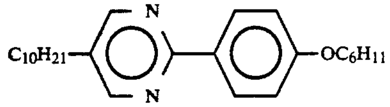
(175)
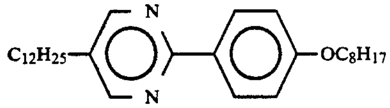
(176)

-continued
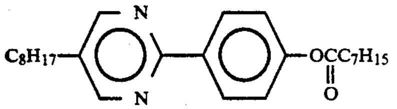
(177)
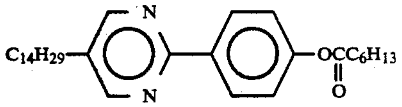
(178)
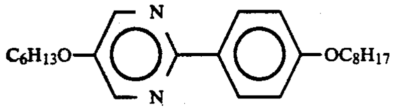
(179)
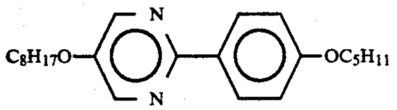
(180)
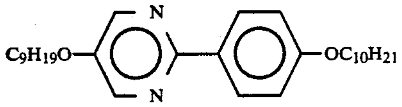
(181)
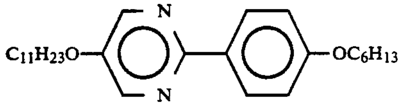
(182)
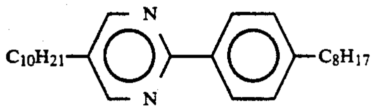
(183)
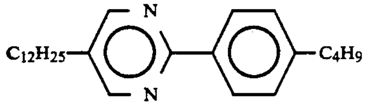
(184)
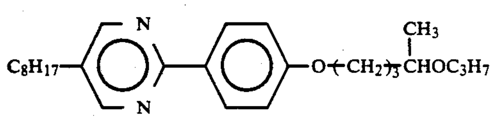
(185)
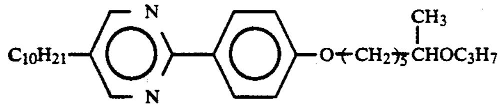
(186)
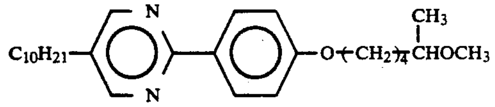
(187)
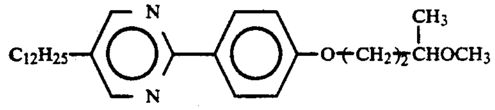
(188)
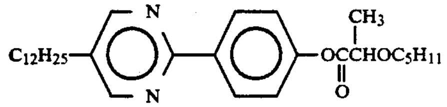
(189)

-continued
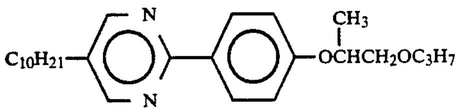
(190)
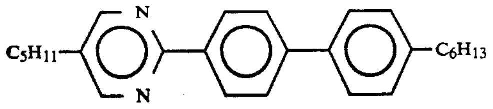
(191)
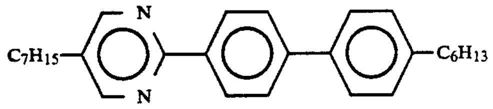
(192)
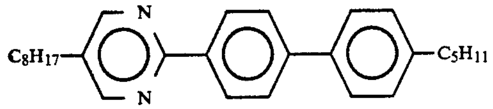
(193)
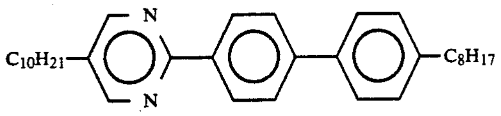
(194)
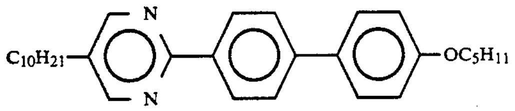
(195)
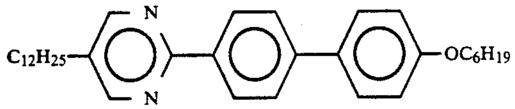
(196)
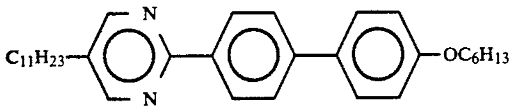
(197)
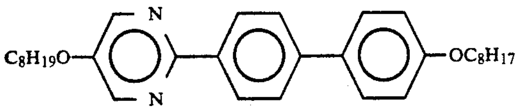
(198)
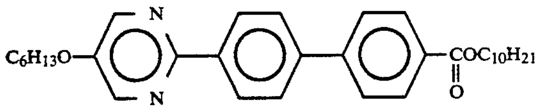
(199)
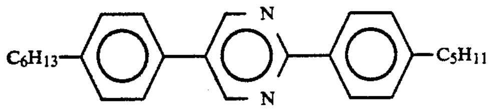
(200)
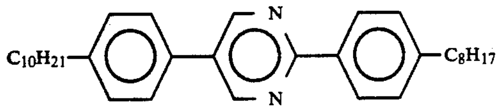
(201)
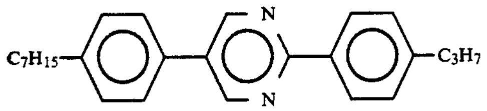
(202)

-continued
(203)
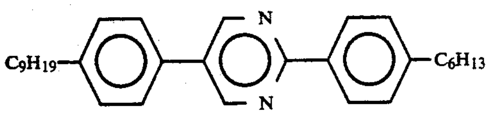
(204)
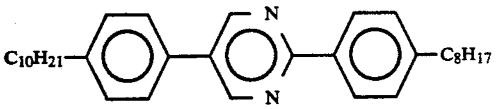
(205)
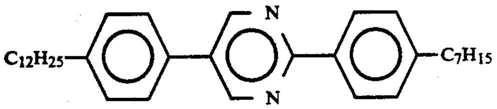
(206)
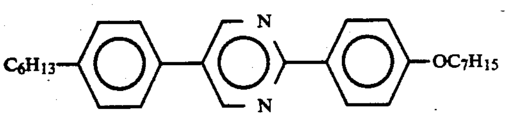
(207)
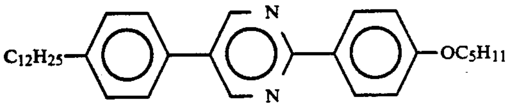
(208)
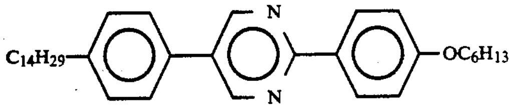
(209)
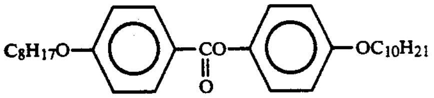
(210)
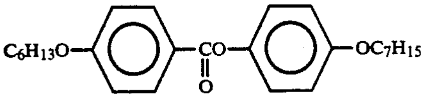
(211)
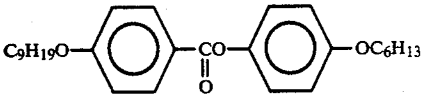
(212)
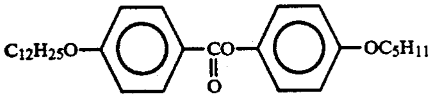
(213)
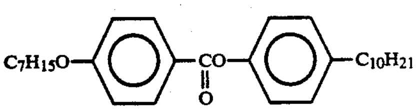
(214)
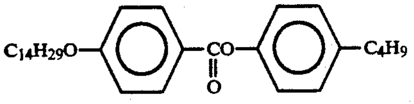
(215)
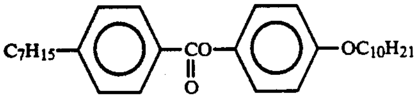

-continued
(216)
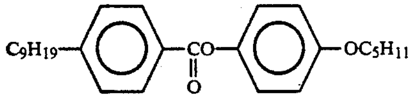
(217)
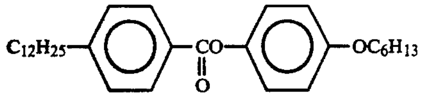
(218)
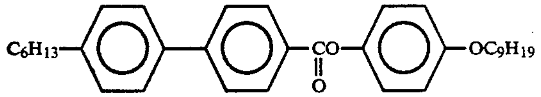
(219)
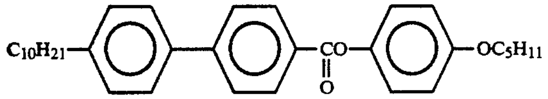
(220)
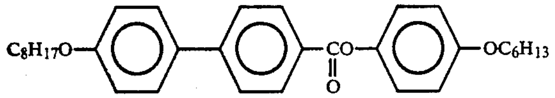
(221)
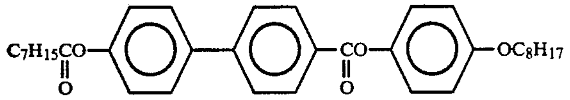
(222)
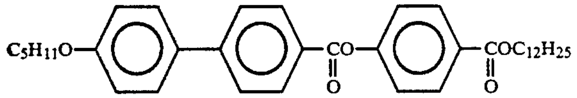
(223)
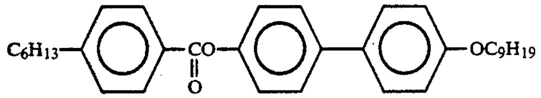
(224)
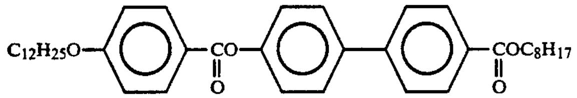
(225)
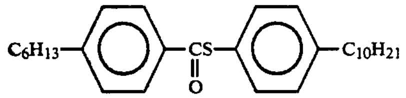
(226)
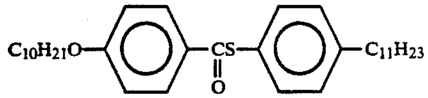
(227)
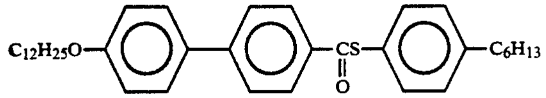
(228)
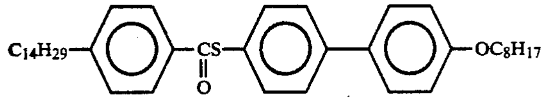
(229)
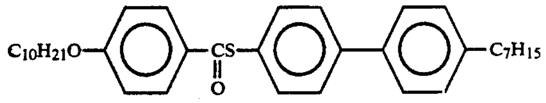

-continued
(230)
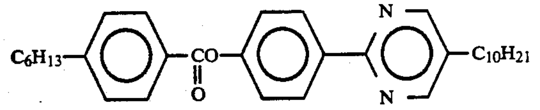
(231)
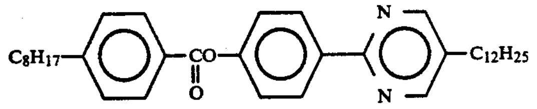
(232)
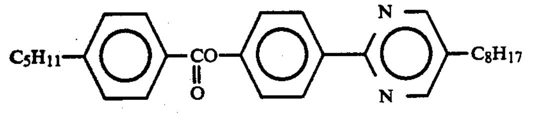
(233)
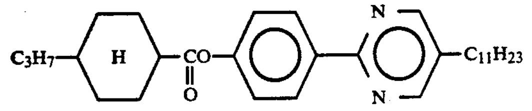
(234)
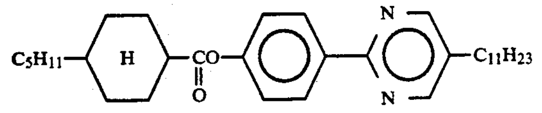
(235)
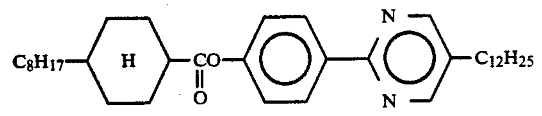
(236)
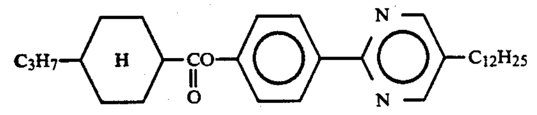
(237)
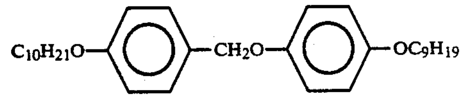
(238)
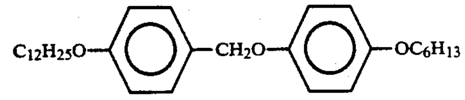
(239)
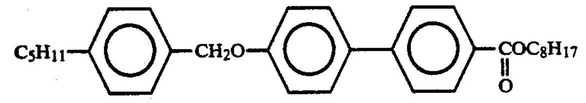
(240)
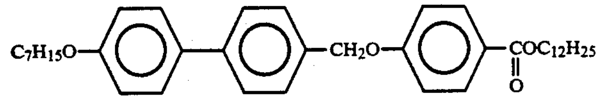
(241)
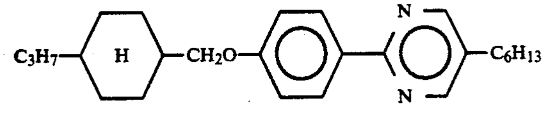
(242)
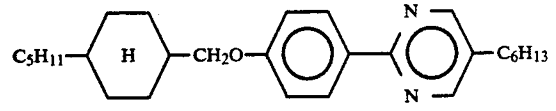

-continued

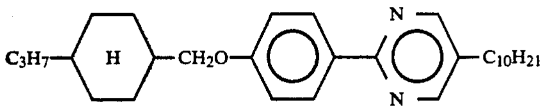
(243)

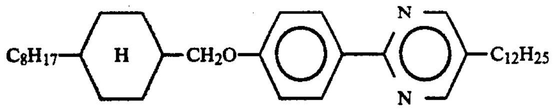
(244)

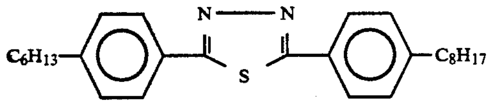
(245)

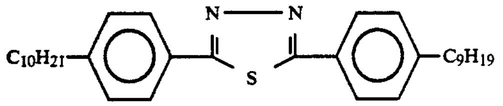
(246)

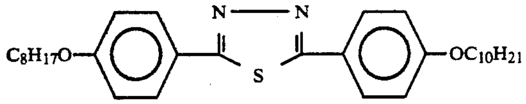
(247)

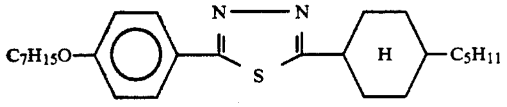
(248)

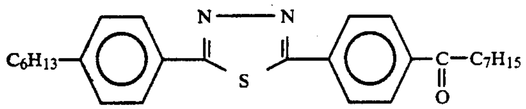
(249)

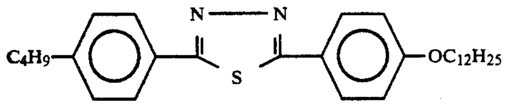
(250)

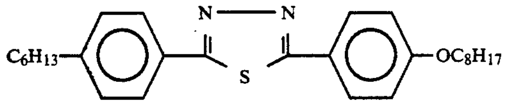
(251)

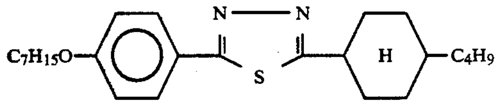
(252)

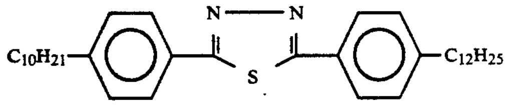
(253)

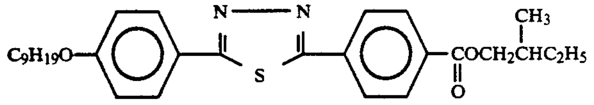
(254)

In formulating the liquid crystal composition according to the present invention, the liquid crystal composition may desirably contain 1-80 wt. %, preferably 1-65 wt. % of a mesomorphic compound represented by the formula (I).

Further, when two or more species of the compounds represented by the formula (I) are used, the liquid crystal composition may desirably contain 1-80 wt. %, preferably 1-65 wt. % of the two or more species of the compounds represented by the formula (I).

The ferroelectric liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the ferroelectric liquid crystal device prepared as described above for explanation of the structure thereof.

Referring to FIG. 1, the ferroelectric liquid crystal device includes a ferroelectric liquid crystal layer 1 disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer may have a thickness of ordinarily 30 Å–1 micron, preferably 30–3000 Å, further preferably 50–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer 1 in a thickness of generally 0.5 to 20 microns, preferably 1 to 5 microns.

The ferroelectric liquid crystal provided by the composition of the present invention may desirably assume a SmC* phase (chiral smectic C phase) in a wide temperature range including room temperature (particularly, broad in a lower temperature side) and also shows wide drive voltage margin and drive temperature margin when contained in a device.

Particularly, in order to show a good alignment characteristic to form a uniform monodomain, the ferroelectric liquid crystal may show a phase transition series comprising isotropic phase—Ch phase (cholesteric phase)—SmA phase (smectic A phase)—SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
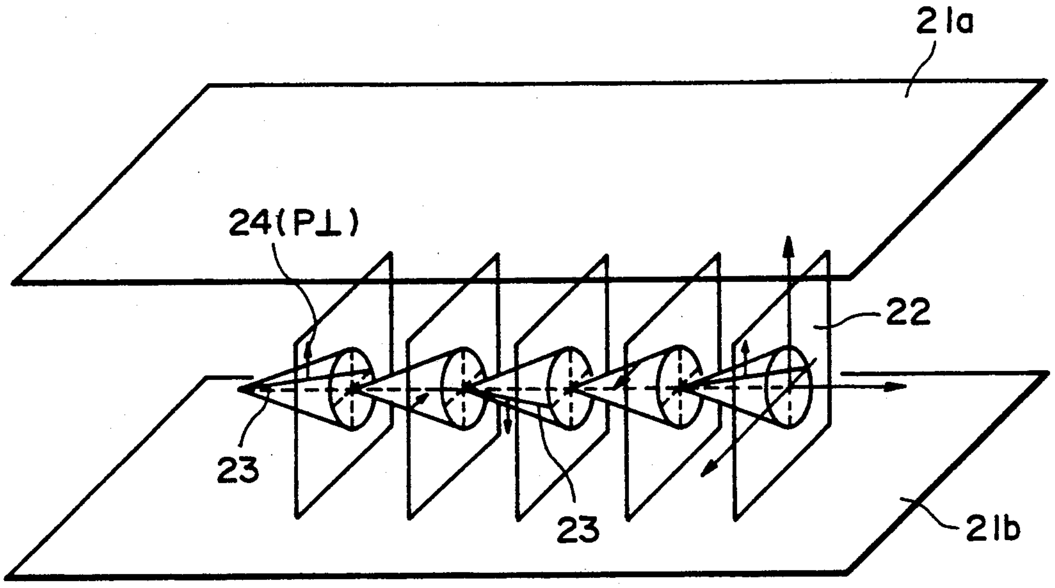
FIGS. 2 and 3 are schematic perspective views of a device cell embodiment for illustrating the operation principle of a ferroelectric liquid crystal device.

FIG. 2 is a schematic illustration of a ferroelectric liquid crystal cell (device) for explaining operation thereof. Reference numerals 21*a* and 21*b* denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment ($P\perp$) 24 in a direction perpendicular to the axis thereof. The liquid crystal molecules 23 continuously form a helical structure in the direction of extension of the substrates. When a voltage higher than a certain threshold level is applied between electrodes formed on the substrates 21*a* and 21*b*, a helical structure of the liquid crystal molecule 23 is unwound or released to change the alignment direction of respective liquid crystal molecules 23 so that the dipole moments ($P\perp$) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
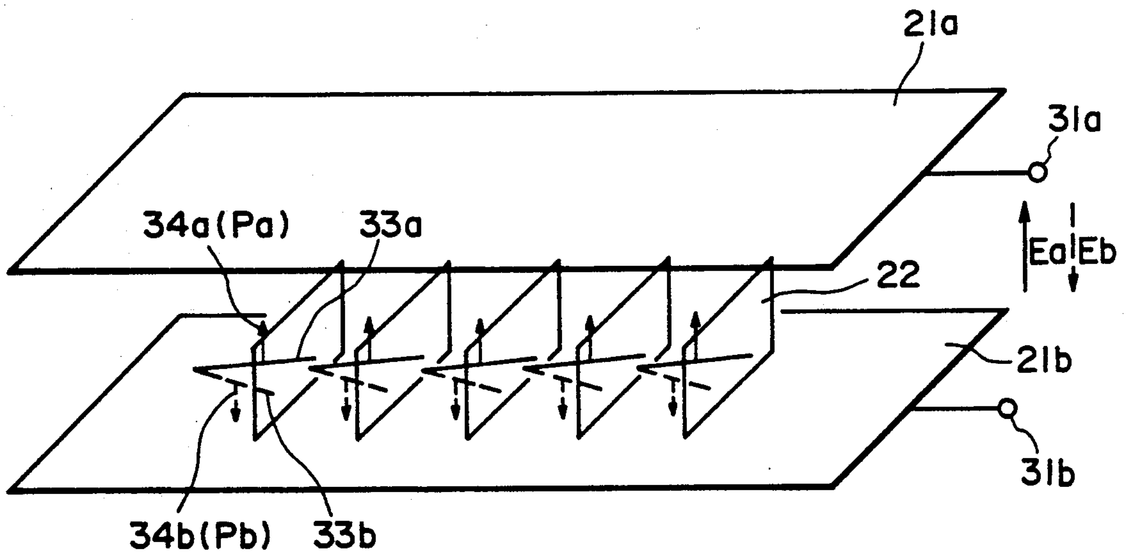

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34*a* or Pb in a lower direction 34*b* as shown in FIG. 3, thus providing a bistable condition. When an electric field Ea or Eb higher than a certain threshold level and different from each other in polarity as shown in FIG. 3 is applied to a cell having the above-mentioned characteristics, the dipole moment is directed either in the upper direction 34*a* or in the lower direction 34*b* depending on the vector of the electric field Ea or Eb. In correspondence with this, the liquid crystal molecules are oriented in either of a first stable state 33*a* and a second stable state 33*b*.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33*a*. This state is stably retained even if the electric field is removed. On the other hand, when the electric field Eb of which direction is opposite to that of the electric field Ea is applied thereto, the liquid crystal molecules are oriented to the second stable state 33*b*, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

When such a ferroelectric liquid crystal device comprising a ferroelectric liquid crystal composition as described above between a pair of electrode plates is constituted as a simple matrix display device, the device may be driven by a driving method as disclosed in Japanese Laid-Open Patent Applications (KOKAI) Nos. 193426/1984, 193427/1984, 156046/1985, 156047/1985, etc.

Hereinbelow, the present invention will be explained more specifically with reference to examples. It is however to be understood that the present invention is not restricted to these examples.

EXAMPLE 1

2-(5-butyl-2-pyridyl)-5-(4-dodecyloxyphenyl)-1,3,4-thiadiazole (Example Compound No. 1—1) was synthesized through the following steps i)–v).

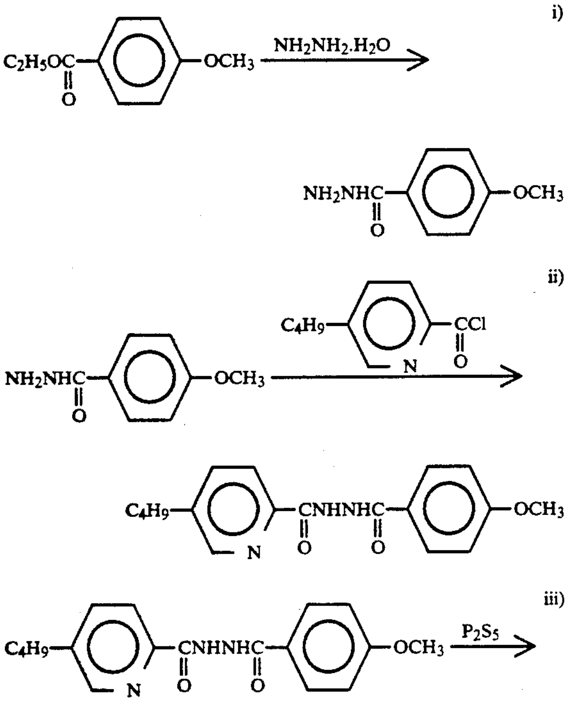

-continued

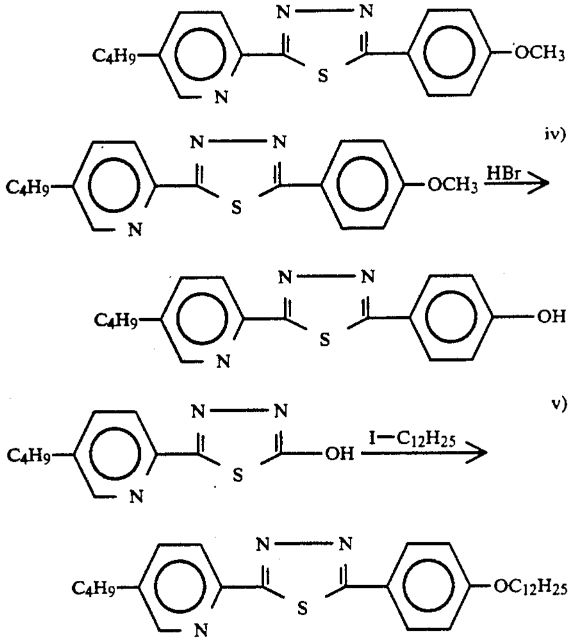

Step 1) Production of 4-methoxybenzohydrazide 303 g of hydrazine hydrate was added to a solution of 150 g of p-ethylanisic acid in 300 ml of ethanol, followed by heat-refluxing for 20 hours. After the reaction, the reaction mixture was poured into 1.5 liters of iced water to precipitate a crystal. The crystal was recrystallized from ethanol to obtain 88.2 g of 4-methoxybenzohydrazide.

Step ii) Production of N-(5-butyl-2-pyridino)-N'-4-methoxybenzodihydrazide 16.4 g of 4-methoxybenzohydrazide was dissolved in 160 ml of pyridine and heated to 40° C. To the above solution, a solution of 9.9 g of 5-butyl-2-pyridinecarbonyl chloride in 47 ml of dry benzene was added dropwise. The mixture was reacted for 16 hours at 40° C., followed by distilling-off of benzene alone to obtain a crude objective product. The resultant objective product was subjected to the following step without purification.

Step iii) Production of 2-(5-butyl-2-pyridyl)-5-(4-methoxyphenyl)-1,3,4-thiadiazole To the above-prepared solution of N-(5-butyl-2l-pyridino)-N'-4-methoxybenzodihydrazide in pyridine, 14.5 g of diphosphorus pentasulfide was added at room temperature, followed by heating to 100° C. for 5 hours of reaction. After the reaction, the reaction mixture was poured into a mixture solution of 40 ml of ethanol and 400 ml of water to precipitate a crystal. The resultant crystal was purified by column chromatography (mobile phase: chloroform/ethyl acetate=20/1, stationary phase: silica gel) to obtain 9.2 g of an objective product.

Step iv) Production of 2-(5-butyl-2-pyridyl)-5-(4-hydroxyphenyl)-1,3,4-thiadiazole To 9.0 g of 2-(5-butyl-2-pyridyl)-5-(4-methoxyphenyl)-1,3,4-thiadiazole, 90 g of a solution of hydrogen bromide in acetic acid was added, followed by heating to 100° C. for 95 hours of reaction while gaseous hydrogen bromide was bubbled. After the reaction, the reaction mixture was poured into 1 liter of water to precipitate a crystal. The crystal was washed with water and recrystallized from a mixture solvent of ethanol/water=9/1 to obtain 2.8 g of an objective product.

Step v) Production of 2-(5-butyl-2l-pyridyl)-5-(4-dodecyloxyphenyl)-1,3,4-thiadiazole To a solution of 0.6 g of 2-(5-butyl-2-pyridyl)-5-(4-hydroxyphenyl)-1-3,4-thiadiazole in 20 ml of N,N-dimethylformamide, 0.15 g of 85% potassium hydroxide was added, followed by stirring for 30 min. at 110° C. To the mixture, 0.69 g of dodecyl iodide was added, followed by stirring for 5 hours at 110° C. After the reaction, the reaction mixture was subjected to filtration to provide a crystal. The resultant crystal was washed with water and recrystallized from ethyl acetate to obtain 0.47 g of 2-(5-butyl-2-pyridyl)-5-(4-dodecyloxyphenyl)-1,3,4-thiadiazole.

Phase transition temperature (°C.)

-continued $$\text{Cry.} \underset{135.8}{\overset{140.9}{\rightleftarrows}} \text{N} \underset{142.2}{\overset{143.2}{\rightleftarrows}} \text{Iso.}$$

Cry.: crystal,
N: nematic phase, and
Iso.: isotropic phase.

EXAMPLE 2

2-(5-butyl-2-pyridyl)-5-(4-octyloxyphenyl)-1,3,4-thiadiazole (Example Compound No. 1-57) was synthesized in the following manner.

The above compound was prepared in the same manner as in Example 1 except that octyl iodide was used instead of dodecyl iodide in Step v) of Example 1.

Phase transition temperature (°C.)

$$\text{Cry.} \underset{136.0}{\overset{141.3}{\rightleftarrows}} \text{N} \underset{151.6}{\overset{152.4}{\rightleftarrows}} \text{Iso.}$$

EXAMPLE 3

A liquid crystal composition A was prepared by mixing the following compounds in respectively indicated proportions.

| Ex. Comp. No. | Structural formula | wt. parts |
|---|---|---|
| 20 | 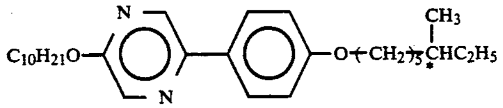 | 15 |
| 21 | 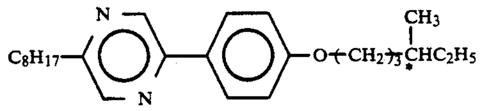 | 15 |
| 58 | 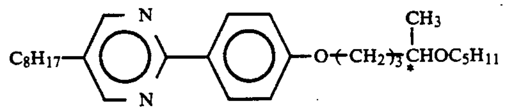 | 10 |
| 89 | 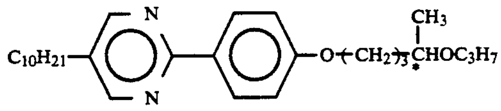 | 20 |
| 120 | 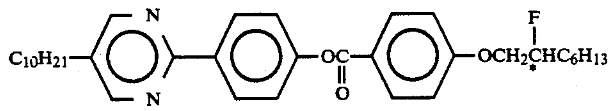 | 13 |
| 129 | 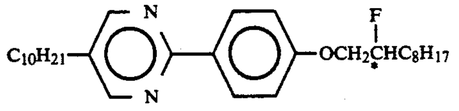 | 7 |
| 236 | 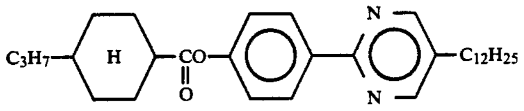 | 15 |

-continued

| Ex. Comp. No. | Structural formula | wt. parts |
|---|---|---|
| 242 | 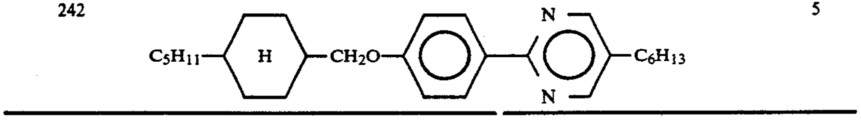 | 5 |

mixed with the following Example compounds in the proportions indicated below to provide a liquid crystal composition B.

| Ex. Comp. No. | Structural formula | wt. parts |
|---|---|---|
| 1-1 | 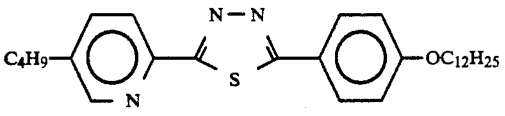 | 5 |
| 1-2 | 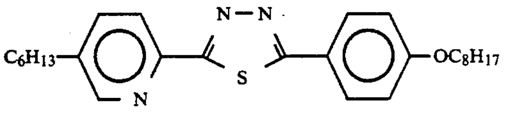 | 5 |
| | Composition A | 90 |

Then, two 0.7 mm-thick glass plates were provided and respectively coated with an ITO film to form an electrode for voltage application, which was further coated with an insulating layer of vapor-deposited $SiO_2$. On the insulating layer, a 0.2 %-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B prepared in Example 3 was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of an optical response time (time from voltage application until the transmittance change reaches 90% of the maximum under the application of a peak-to-peak voltage Vpp of 20V in combination with right-angle cross-nicol polarizers).

The results are shown below.

| | 15° C. | 25° C. | 35° C. |
|---|---|---|---|
| Response time (μsec) | 136 | 94 | 82 |

COMPARATIVE EXAMPLE 1

A ferroelectric liquid crystal device was prepared in the same manner as in Example 3 except that the liquid crystal composition A prepared in Example 3 was injected into a cell. The measured values of the response time of the device were as follows.

| | 15° C. | 25° C. | 35° C. |
|---|---|---|---|
| Response time (μsec) | 155 | 100 | 80 |

EXAMPLE 4

A liquid crystal composition C was prepared in the same manner as in Example 3 except that the following Example compounds were used instead of Example Compounds Nos. 1-1 and 1-2 in respectively indicated proportions.

| Ex. Comp. No. | Structural formula | wt. parts |
|---|---|---|
| 1-6 | 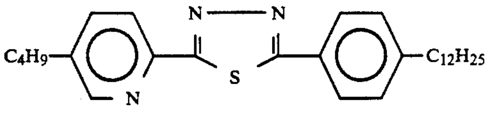 | 3 |

-continued

| Ex. Comp. No. | Structural formula | wt. parts |
|---|---|---|
| 1-25 | 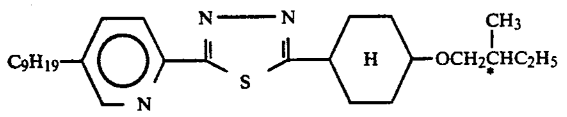 | 3 |
| 1-39 | 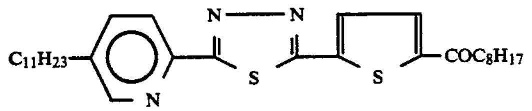 | 3 |
| | Composition A | 91 |

A ferroelectric liquid crystal device was prepared in the same manner as in Example 3 except for using the composition C. The ferroelectric liquid crystal device was subjected to measurement of response time, whereby the following results were obtained.

| | 15° C. | 25° C. | 35° C. |
|---|---|---|---|
| Response time (μsec) | 140 | 99 | 85 |

EXAMPLE 5

A liquid crystal composition D was prepared in the same manner as in Example 3 except that the following Example Compounds were used instead of Example Compounds Nos. 1—1 and 1-2 in respectively indicated proportions.

| Ex. Comp. No. | Structural formula | wt. parts |
|---|---|---|
| 1-45 | 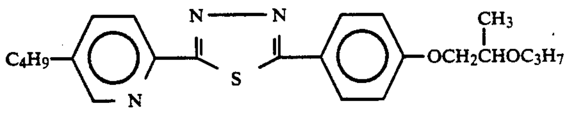 | 3 |
| 1-56 | 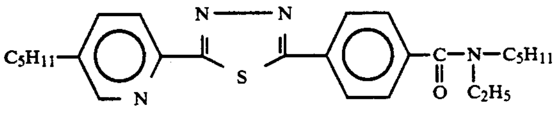 | 2 |
| 1-66 | 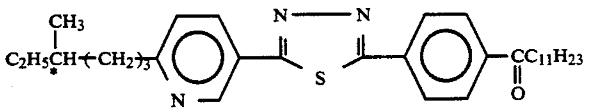 | 2 |
| 1-90 | 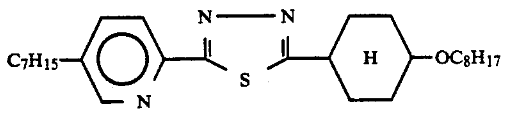 | 3 |
| | Composition A | 90 |

A ferroelectric liquid crystal device was prepared in the same manner as in Example 3 except for using the composition D. The ferroelectric liquid crystal device was subjected to measurement of response time, whereby the following results were obtained.

| | 15° C. | 25° C. | 35° C. |
|---|---|---|---|
| Response time (μsec) | 138 | 100 | 87 |

EXAMPLE 6

A liquid crystal composition E was prepared in the same manner as in Example 3 except that the following Example Compounds were used instead of Example Compounds Nos. 1—1 and 1-2 in respectively indicated proportions.

| Ex. Comp. No. | Structural formula | wt. parts |
|---|---|---|
| 1-15 | 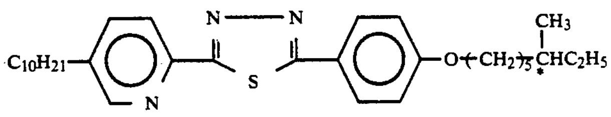 | 2 |

-continued

| Ex. Comp. No. | Structural formula | wt. parts |
|---|---|---|
| 1-86 | 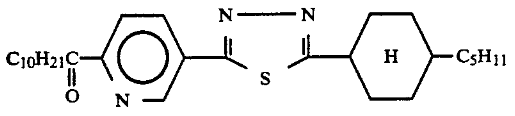 | 2 |
| 1-104 | 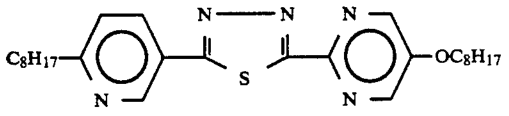 | 3 |
| 1-115 | 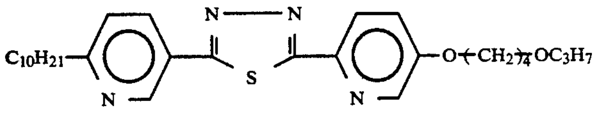 | 3 |
| | Composition A | 90 |

A ferroelectric liquid crystal device was prepared in the same manner as in Example 3 except for using the composition E. The ferroelectric liquid crystal device was subjected to measurement of response time, whereby the following results were obtained.

| | 15° C. | 25° C. | 35° C. |
|---|---|---|---|
| Response time (μsec) | 132 | 96 | 79 |

EXAMPLE 7

A liquid crystal composition F was prepared in the same manner as in Example 3 except that the following Example Compounds were used instead of Example Compounds Nos. 1—1 and 1-2 in respectively indicated proportions.

| Ex. Comp. No. | Structural formula | wt. parts |
|---|---|---|
| 1-11 | 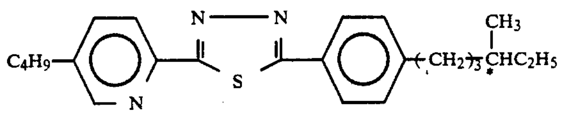 | 2 |
| 1-27 | 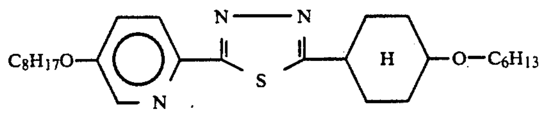 | 2 |
| 1-47 | 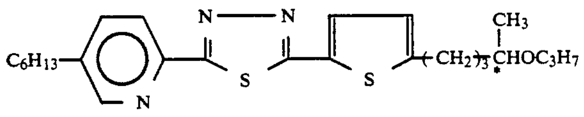 | 2 |
| 1-70 | 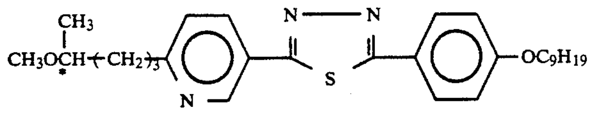 | 3 |
| | Composition A | 91 |

A ferroelectric liquid crystal device was prepared in the same manner as in Example 3 except for using the composition F. The ferroelectric liquid crystal device was subjected to measurement of response time, whereby the following results were obtained.

| | 15° C. | 25° C. | 35° C. |
|---|---|---|---|
| Response time (μsec) | 118 | 87 | 74 |

EXAMPLE 8

A liquid crystal composition G was prepared by mixing the following compounds in respectively indicated proportions.

| Ex. Comp. No. | Structural formula | wt. parts |
|---|---|---|
| 8 | 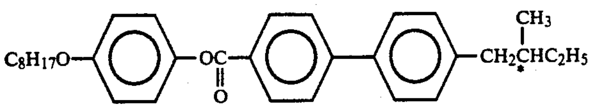 | 16 |
| 9 | 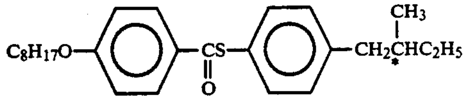 | 22.5 |
| 18 | 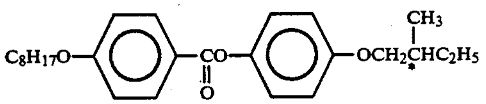 | 64 |
| 23 | 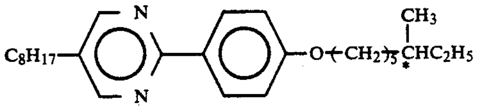 | 10 |
| 24 | 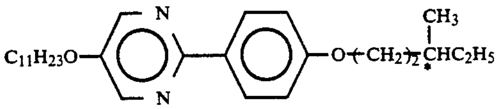 | 10 |
| 43 | 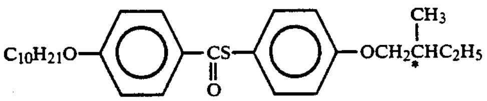 | 22.5 |
| 63 | 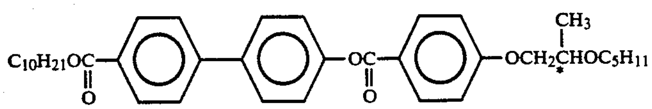 | 15 |
| 87 | 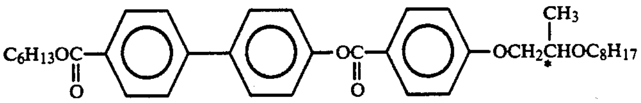 | 15 |
| 124 | 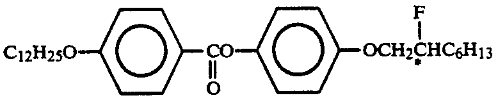 | 6.75 |
| 136 | 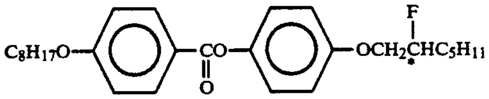 | 18.75 |
| 236 | 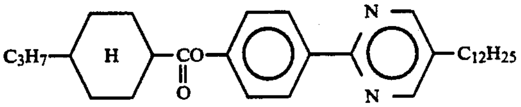 | 20 |
The liquid crystal composition G was further mixed with the following Example compounds in the proportions indicated below to provide a liquid crystal composition H.

| Ex. Comp. No. | Structural formula | wt. parts |
|---|---|---|
| 1-7 | 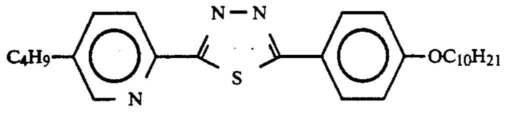 | 3 |
| 1-23 | 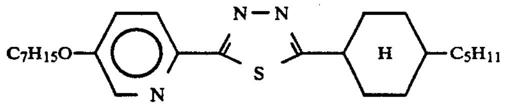 | 4 |
| 1-80 | 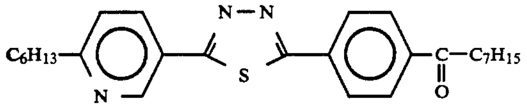 | 4 |
| | Composition G | 89 |

A ferroelectric liquid crystal device was prepared in the same manner as in Example 3 except for using the composition H. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 314 | 213 | 170 |

COMPARATIVE EXAMPLE 2

A ferroelectric liquid crystal device was prepared in the same manner as in Example 3 except that the liquid crystal composition G prepared in Example 3 was injected into a cell. The measured values of the response time of the device were as follows.

| | 15° C. | 25° C. | 35° C. |
|---|---|---|---|
| Response time (μsec) | 450 | 270 | 195 |

EXAMPLE 9

A liquid crystal composition I was prepared in the same manner as in Example 8 except that the following Example Compounds were used instead of Example Compounds Nos. 1-13, 1-55 and 1-80 in respectively indicated proportions.

| Ex. Comp. No. | Structural formula | wt. parts |
|---|---|---|
| 1-1 | 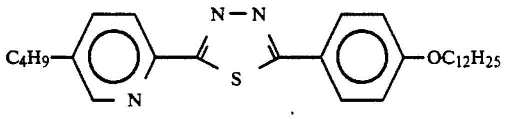 | 3 |
| 1-10 | 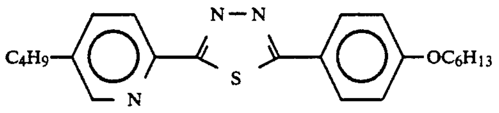 | 3 |
| 1-109 | 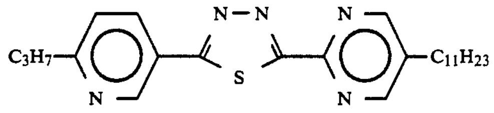 | 2 |
| 1-119 | 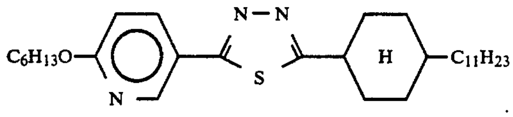 | 2 |
| | Composition G | 90 |

A ferroelectric liquid crystal device was prepared in the same manner as in Example 3 except for using the composition I. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 317 | 222 | 174 |

Further, when the device was driven, a clear switching action was observed, and good bistability was shown after the termination of the voltage application.

EXAMPLE 10

A liquid crystal composition J was prepared in the same manner as in Example 8 except that the following Example Compounds were used instead of Example Compounds Nos. 1-13, 1-55 and 1-80 in respectively indicated proportions.

| Ex. Comp. No. | Structural formula | wt. parts |
|---|---|---|
| 1-33 | 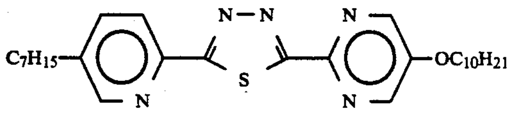 | 3 |
| 1-53 | 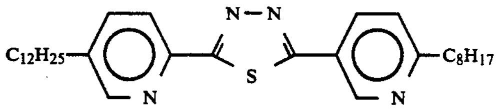 | 3 |
| 1-83 | 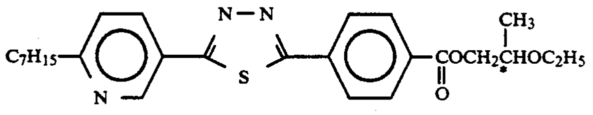 | 2 |
| 1-98 | 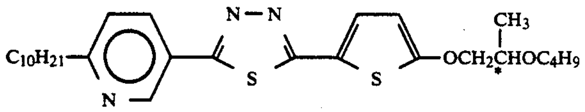 | 2 |
| | Composition G | 90 |

A ferroelectric liquid crystal device was prepared in the same manner as in Example 3 except for using the composition J. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 311 | 217 | 171 |

Further, when the device was driven, a clear switching action was observed, and good bistability was shown after the termination of the voltage application.

EXAMPLE 11

A liquid crystal composition K was prepared in the same manner as in Example 8 except that the following Example Compounds were used instead of Example Compounds Nos. 1-13, 1-55 and 1-80 in respectively indicated proportions.

| Ex. Comp. No. | Structural formula | wt. parts |
|---|---|---|
| 1-78 | 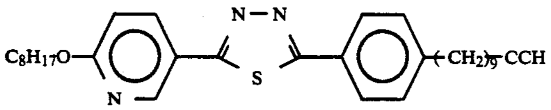 | 3 |
| 1-94 | 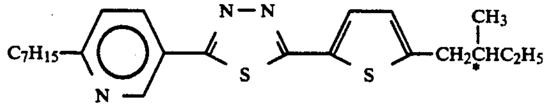 | 2 |
| 1-99 | 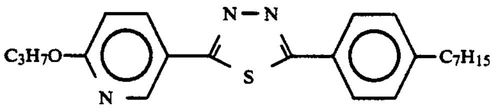 | 2 |
| 1-115 | 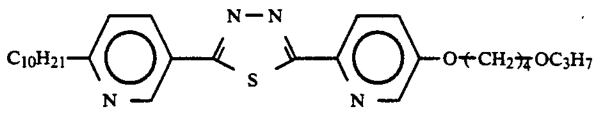 | 2 |

-continued

| Ex. Comp. No. | Structural formula | wt. parts |
|---|---|---|
| | Composition G | 90 |

A ferroelectric liquid crystal device was prepared in the same manner as in Example 3 except for using the composition K. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 318 | 215 | 170 |

Further, when the device was driven, a clear switching action was observed, and good bistability was shown after the termination of the voltage application.

EXAMPLE 12

A liquid crystal composition L was prepared in the same manner as in Example 8 except that the following Example Compounds were used instead of Example Compounds Nos. 1-13, 1-55 and 1-80 in respectively indicated proportions.

| Ex. Comp. No. | Structural formula | wt. parts |
|---|---|---|
| 1-69 | 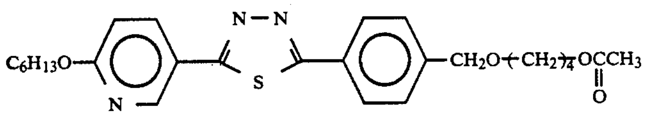 | 2 |
| 1-89 | 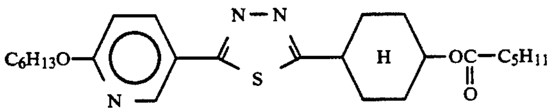 | 2 |
| 1-104 | 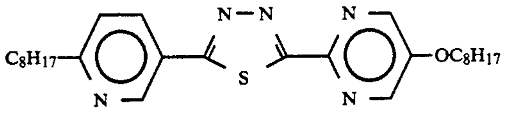 | 2 |
| 1-116 | 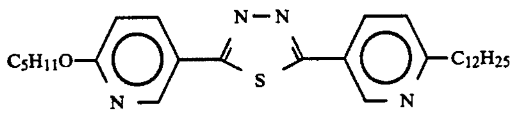 | 2 |
| 1-120 | 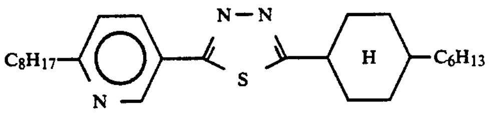 | 2 |
| | Composition G | 90 |

A ferroelectric liquid crystal device was prepared in the same manner as in Example 3 except for using the composition L. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

| | 15° C. | 25° C. | 35° C. |
|---|---|---|---|
| Response time (μsec) | 319 | 225 | 178 |

Further, when the device was driven, a clear switching action was observed, and good bistability was shown after the termination of the voltage application.

EXAMPLES 13-20

Liquid crystal compositions M to T were prepared by replacing the Example Compounds and the liquid crystal compositions used in Example 3 with Example Compounds and liquid crystal compositions shown in the following Table 1. Ferroelectric liquid crystal devices were prepared in the same manner as in Example 3 by respectively using these compositions instead of the composition B, and subjected to measurement of optical response time and observation of switching states. In the devices, a monodomain with a good and uniform alignment characteristic was observed. The results of the measurement are shown in the following Table 1.

TABLE 1

| Ex. No. (Comp. Name) | Example Compound No. or liquid crystal composition name (weight parts) | | | | | | Response time (μsec) 15° C. | 25° C. | 35° C. |
|---|---|---|---|---|---|---|---|---|---|
| 13 | 1-1 | 1-3 | 1-72 | 1-84 | | A | 134 | 98 | 86 |
| (M) | 2 | 2 | 3 | 2 | | 91 | | | |
| 14 | 1-14 | 1-61 | 1-91 | 1-101 | | A | 137 | 96 | 83 |
| (N) | 2 | 2 | 2 | 2 | | 92 | | | |
| 15 | 1-19 | 1-59 | 1-73 | 1-93 | 1-109 | A | 136 | 101 | 89 |
| (O) | 2 | 1 | 1 | 2 | 2 | 92 | | | |
| 16 | 1-27 | 1-47 | 1-67 | 1-100 | 1-113 | A | 135 | 99 | 89 |
| (P) | 2 | 2 | 2 | 1 | 2 | 91 | | | |
| 17 | 1-2 | 1-14 | 1-23 | 1-111 | | G | 314 | 216 | 172 |
| (Q) | 2 | 2 | 2 | 2 | | 92 | | | |
| 18 | 1-30 | 1-35 | 1-70 | 1-92 | | G | 327 | 219 | 169 |
| (R) | 2 | 2 | 3 | 2 | | 91 | | | |
| 19 | 1-58 | 1-65 | 1-90 | 1-114 | 1-119 | G | 313 | 223 | 174 |
| (S) | 2 | 2 | 2 | 2 | 2 | 90 | | | |
| 20 | 1-6 | 1-13 | 1-36 | 1-61 | 1-110 | G | 329 | 224 | 176 |
| (T) | 2 | 2 | 3 | 1 | 2 | 90 | | | |

As is apparent from the results shown in the above Examples 13-20, the ferroelectric liquid crystal devices containing the liquid crystal compositions M to T showed an improved low-temperature operation characteristic, a high speed responsiveness, and a decreased temperature dependence of the response speed.

EXAMPLE 21

A liquid crystal composition U was prepared in the same manner as in Example 3 except that the following Example Compounds were used instead of Example Compounds Nos. 1—1 and 1-2 in respectively indicated proportions.

| Ex. Comp. No. | Structural formula | wt. parts |
|---|---|---|
| 1-7 | 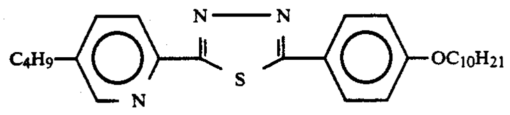 | 2 |
| 1-87 | 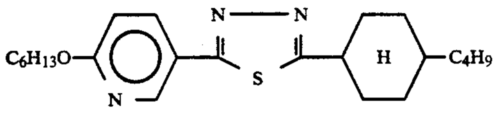 | 3 |
| 247 | 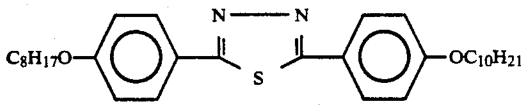 | 2 |
| 251 | 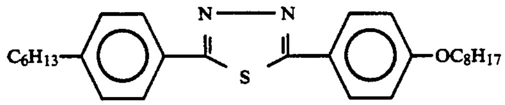 | 3 |
| | Composition A | 90 |

A ferroelectric liquid crystal device was prepared in the same manner as in Example 3 except for using the composition U. The ferroelectric liquid crystal device was subjected to measurement of response time, whereby the following results were obtained.

| | 15° C. | 25° C. | 35° C. |
|---|---|---|---|
| Response time (μsec) | 130 | 95 | 81 |

COMPARATIVE EXAMPLE 3

A liquid crystal composition V was prepared in the same manner as in Example 21 except that the following Example Compounds were used instead of Example Compounds Nos. 1-7, 1-87, 247 and 251 in respectively indicated proportions.

| Ex. Comp. No. | Structural formula | wt. parts |
|---|---|---|
| 247 | 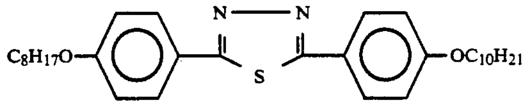 | 2 |

-continued

| Ex. Comp. No. | Structural formula | wt. parts |
|---|---|---|
| 251 | 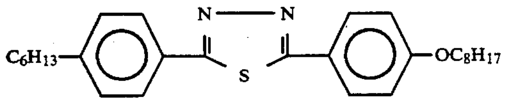 | 3 |
| | Composition A | 90 |

A ferroelectric liquid crystal device was prepared in the same manner as in Example 3 except for using the composition V. The ferroelectric liquid crystal device was subjected to measurement of response time, whereby the following results were obtained.

| | 15° C. | 25° C. | 35° C. |
|---|---|---|---|
| Response time (μsec) | 145 | 100 | 82 |

As is apparent from the above Comparative Example 3 and Example 21, the device using the liquid crystal composition U prepared by mixing the known liquid crystal composition V containing another mesomorphic compound having a thiadiazole ring with a mesomorphic compound of the invention having a thiadiazole ring and a pyridine ring, provided an improved response speed at a lower temperature and also a decreased temperature-dependence of the response speed.

EXAMPLE 22

A liquid crystal composition W was prepared in the same manner as in Example 8 except that the following Example Compounds were used instead of Example Compounds Nos. 1-7, 1-23 and 1-80 in respectively indicated proportions.

| Ex. Comp. No. | Structural formula | wt. parts |
|---|---|---|
| 1-15 | 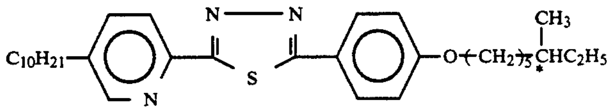 | 3 |
| 1-91 | 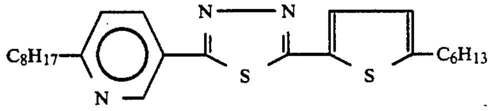 | 2 |
| 246 | 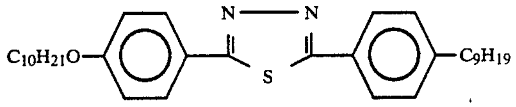 | 3 |
| 252 | 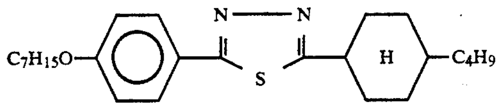 | 2 |
| | Composition G | 90 |

A ferroelectric liquid crystal device was prepared in the same manner as in Example 3 except for using the composition W. The ferroelectric liquid crystal device was subjected to measurement of response time, whereby the following results were obtained.

| | 15° C. | 25° C. | 35° C. |
|---|---|---|---|
| Response time (μsec) | 306 | 213 | 171 |

COMPARATIVE EXAMPLE 4

A liquid crystal composition X was prepared in the same manner as in Example 22 except that the following Example Compounds were used instead of Example Compounds Nos. 1-15, 1-91, 246 and 252 in respectively indicated proportions.

| Ex. Comp. No. | Structural formula | wt. parts |
|---|---|---|
| 246 | 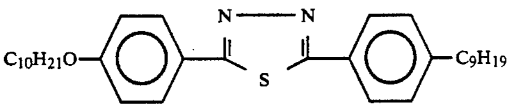 | 3 |

-continued

| Ex. Comp. No. | Structural formula | wt. parts |
|---|---|---|
| 252 | 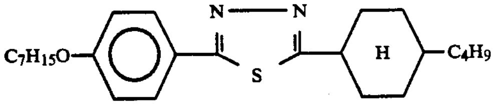 | 2 |
| | Composition G | 90 |

A ferroelectric liquid crystal device was prepared in the same manner as in Example 3 except for using the composition X. The ferroelectric liquid crystal device was subjected to measurement of response time, whereby the following results were obtained.

| | 15° C. | 25° C. | 35° C. |
|---|---|---|---|
| Response time (μsec) | 368 | 242 | 186 |

As is apparent from the above Comparative Example 4 and Example 22, the device using the liquid crystal composition W prepared by mixing the known liquid crystal composition X containing another mesomorphic compound having a thiadiazole ring with a mesomorphic compound of the invention having a thiadiazole ring and a pyridine ring, provided an improved response speed at a lower temperature and also a decreased temperature-dependence of the response speed.

EXAMPLE 23

A blank cell was prepared in the same manner as in Example 3 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition B prepared in Example 3. The liquid crystal device was subjected to measurement of optical response time in the same manner as in Example 3. The results are shown below.

| | 15° C. | 25° C. | 35° C. |
|---|---|---|---|
| Response time (μsec) | 134 | 93 | 81 |

EXAMPLE 24

A blank cell was prepared in the same manner as in Example 3 except for omitting the $SiO_2$ layer to form an alignment control layer composed of the polyimide resin layer alone on each electrode plate. A ferroelectric liquid crystal device was prepared by filling the blank cell with the liquid crystal composition B prepared in Example 3. The liquid crystal device was subjected to measurement of optical response time in the same manner as in Example 3. The results are shown below.

| | 15° C. | 25° C. | 35° C. |
|---|---|---|---|
| Response time (μsec) | 131 | 91 | 79 |

As is apparent from the above Examples 23 and 24, also in the cases of different device structures, the devices containing the ferroelectric liquid crystal composition B according to the present invention respectively provided a remarkably improved operation characteristic at a lower temperature and also a decreased temperature-dependence of the response speed.

As described above, according to the present invention, there are provided a ferroelectric liquid crystal composition and a ferroelectric liquid crystal device containing the composition, which shows a good switching characteristic, an improved low-temperature operation characteristic and a decreased temperature-dependence of response speed.

What is claimed is:

1. A mesomorphic compound represented by the following formula (I):

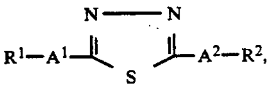

(I)

wherein $R^1$ and $R^2$ respectively denote a linear or branched alkyl group having 1-18 carbon atoms capable of including one or non-neighboring two or more methylene groups which can be replaced with at least one species of —Z—,

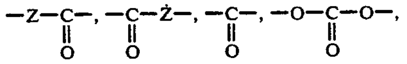

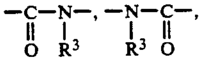

—CH=CH— and —CH≡C—, wherein Z denotes —O— or —S— and $R^3$ denotes hydrogen or an alkyl group having 1-5 carbon atoms; $A^1$ denotes

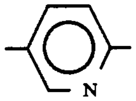 or 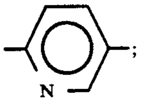;

and $A^2$ denotes any one of

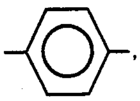, 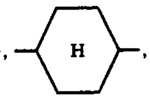, 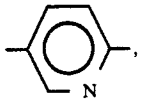,

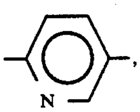, 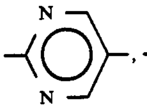, 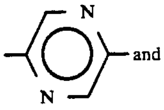 and

-continued

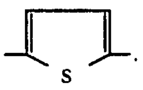

2. A compound according to claim 1, of the formula:

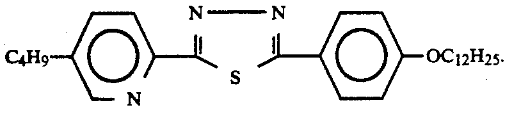

3. A compound according to claim 1, of the formula:

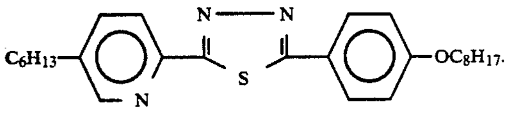

4. A compound according to claim 1, of the formula:

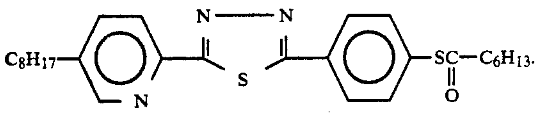

5. A compound according to claim 1, of the formula:

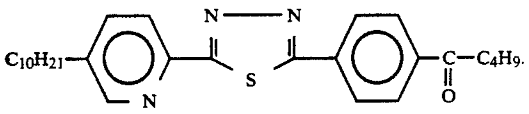

6. A compound according to claim 1, of the formula:

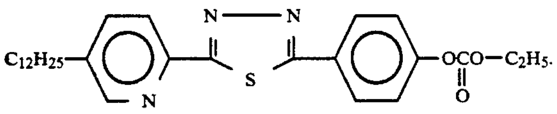

7. A compound according to claim 1, of the formula:

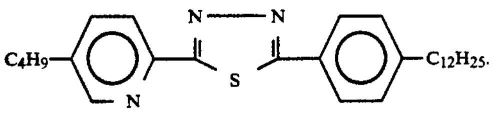

8. A compound according to claim 1, of the formula:

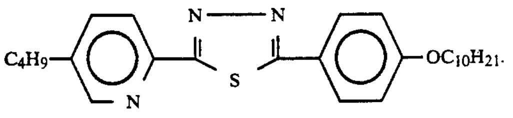

9. A compound according to claim 1, of the formula:

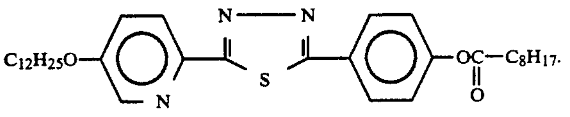

10. A compound according to claim 1, of the formula:

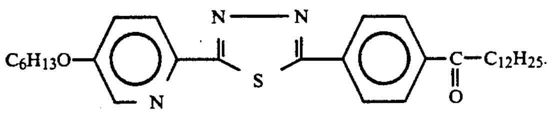

11. A compound according to claim 1, of the formula:

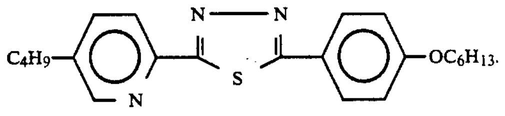

12. A compound according to claim 1, of the formula:

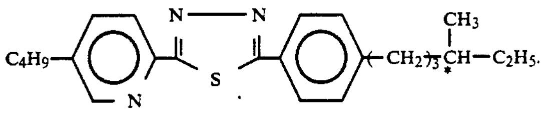

13. A compound according to claim 1, of the formula:

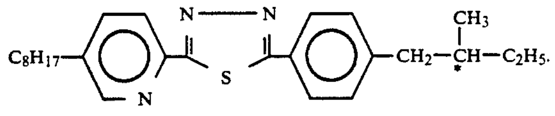

14. A compound according to claim 1, of the formula:

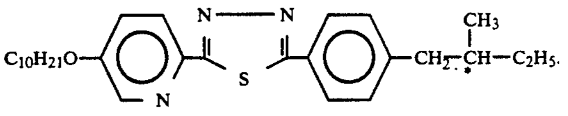

15. A compound according to claim 1, of the formula:

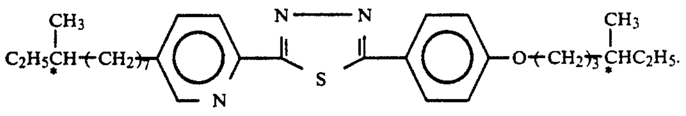

16. A compound according to claim 1, of the formula:

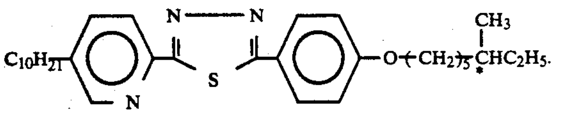

17. A compound according to claim 1, of the formula:

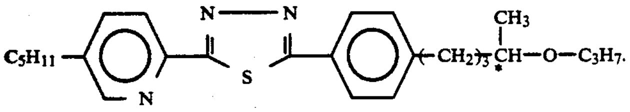

18. A compound according to claim 1, of the formula:

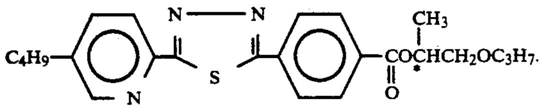

19. A compound according to claim 1, of the formula:

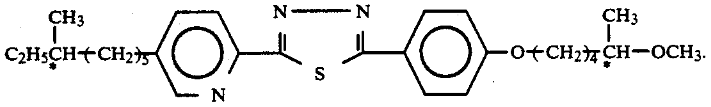

20. A compound according to claim 1, of the formula:

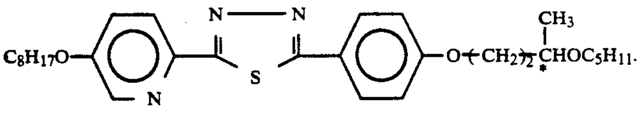

21. A compound according to claim 1, o the formula:

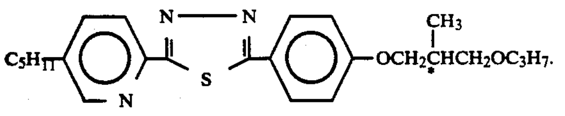

22. A compound according to claim 1, of the formula:

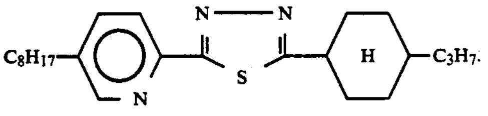

23. A compound according to claim 1, of the formula:

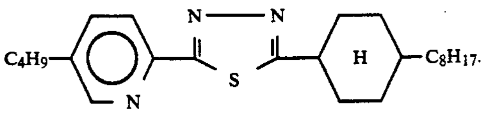

24. A compound according to claim 1, of the formula:

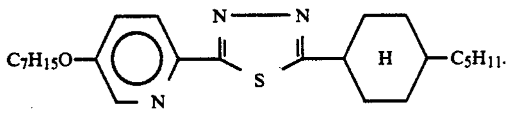

25. A compound according to claim 1, of the formula:

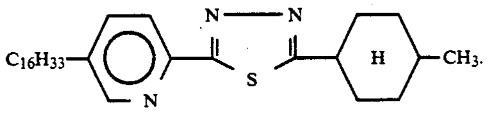

26. A compound according to claim 1, of the formula:

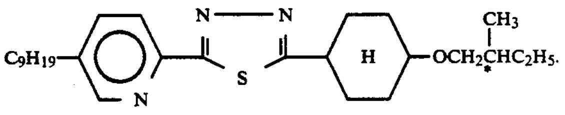

27. A compound according to claim 1, of the formula:

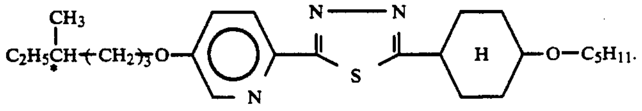

28. A compound according to claim 1, of the formula:

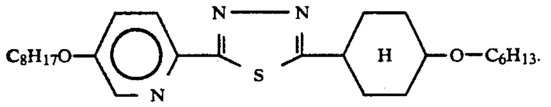

29. A compound according to claim 1, of the formula:

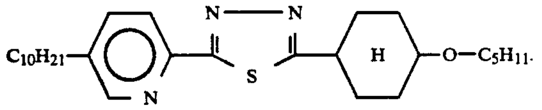

30. A compound according to claim 1, of the formula:

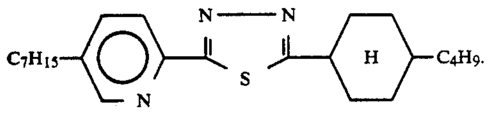

31. A compound according to claim 1, of the formula:

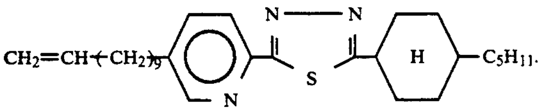

32. A compound according to claim 1, of the formula:

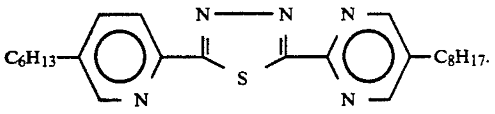

33. A compound according to claim 1, of the formula:

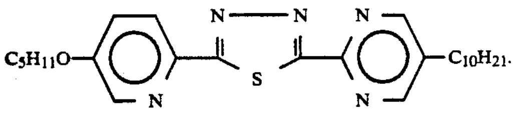

34. A compound according to claim 1, of the formula:

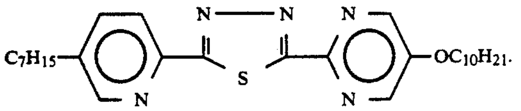

35. A compound according to claim 1, of the formula:

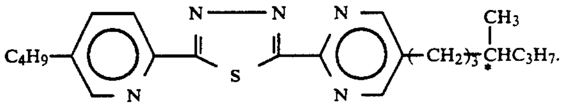

36. A compound according to claim 1, of the formula:

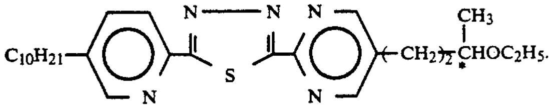

37. A compound according to claim 1, of the formula:

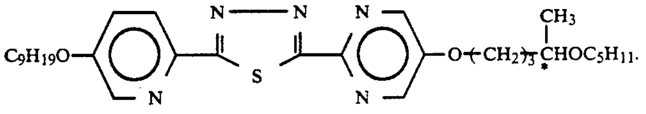

38. A compound according to claim 1, of the formula:

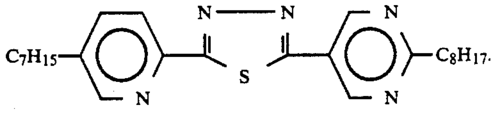

39. A compound according to claim 1, of the formula:

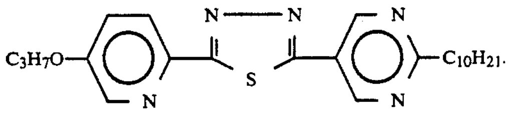

40. A compound according to claim 1, of the formula:

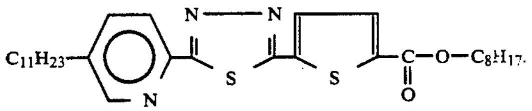

41. A compound according to claim 1, of the formula:

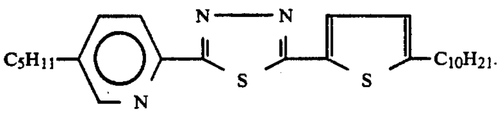

42. A compound according to claim 1, of the formula:

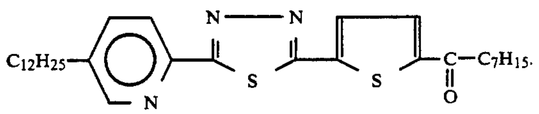

43. A compound according to claim 1, of the formula:

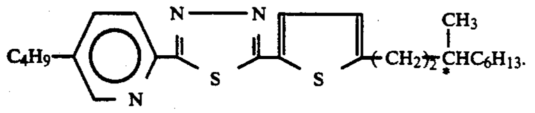

44. A compound according to claim 1, of the formula:

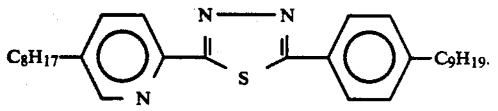

45. A compound according to claim 1, of the formula:

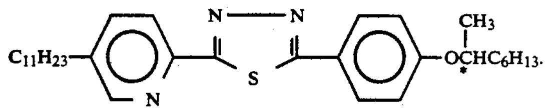

46. A compound according to claim 1, of the formula:

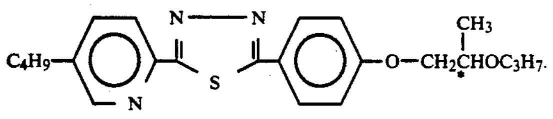

47. A compound according to claim 1, of the formula:

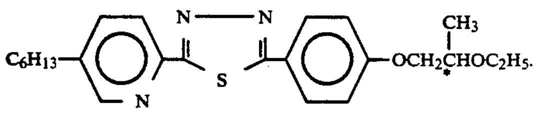

48. A compound according to claim 1, of the formula:

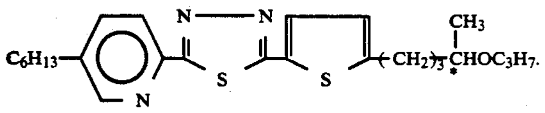

49. A compound according to claim 1, of the formula:

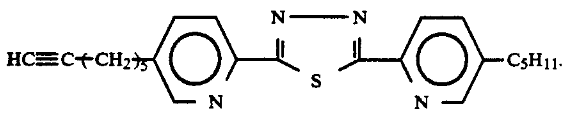

50. A compound according to claim 1, of the formula:

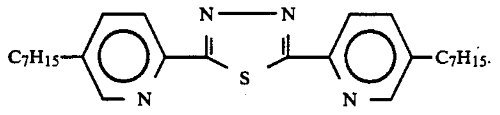

51. A compound according to claim 1, of the formula:

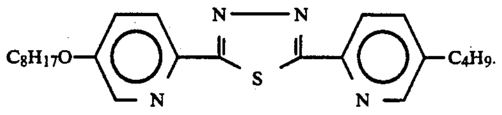

52. A compound according to claim 1, of the formula:

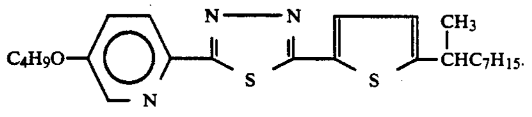

53. A compound according to claim 1, of the formula:

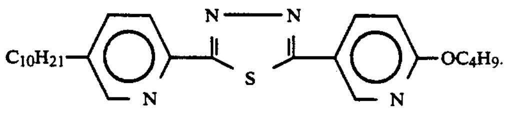

54. A compound according to claim 1, of the formula:

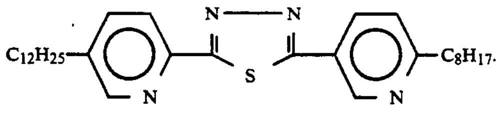

55. A compound according to claim 1, of the formula:

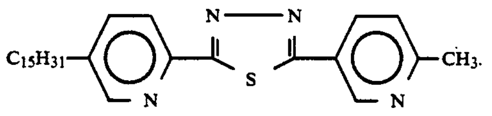

56. A compound according to claim 1, of the formula:

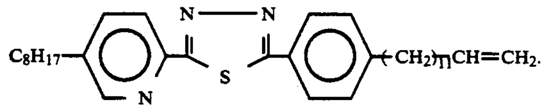

57. A compound according to claim 1, of the formula:

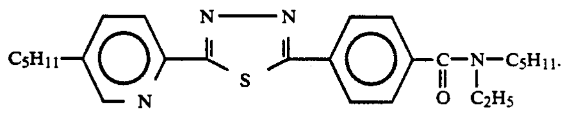

58. A compound according to claim 1, of the formula:

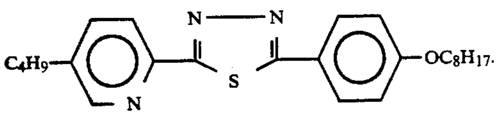

59. A compound according to claim 1, of the formula:

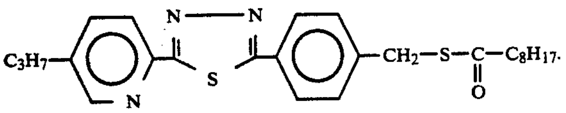

60. A compound according to claim 1, of the formula:

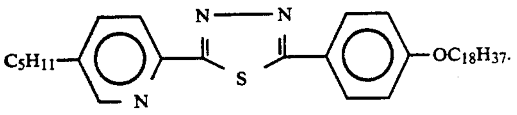

61. A compound according to claim 1, of the formula:

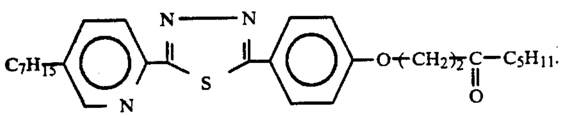

62. A compound according to claim 1, of the formula:

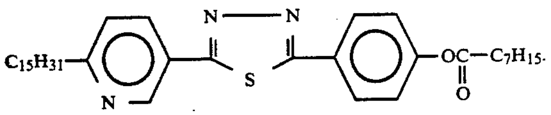

63. A compound according to claim 1, of the formula:

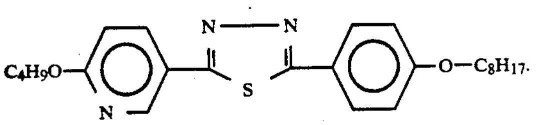

64. A compound according to claim 1, of the formula:

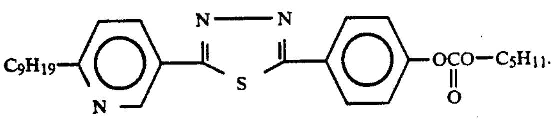

65. A compound according to claim 1, of the formula:

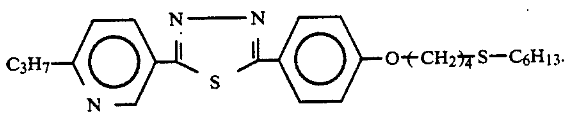

66. A compound according to claim 1, of the formula:

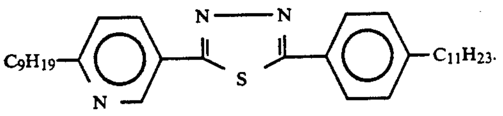

67. A compound according to claim 1, of the formula:

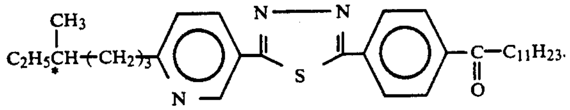

68. A compound according to claim 1, of the formula:

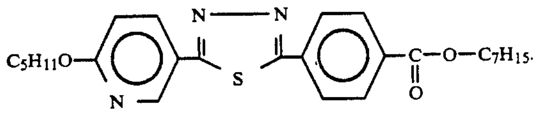

69. A compound according to claim 1, of the formula:

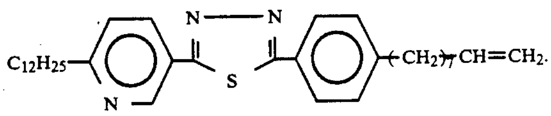

70. A compound according to claim 1, of the formula:

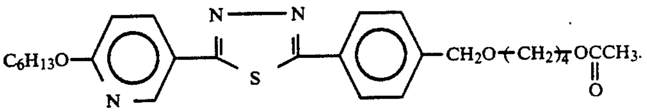

71. A compound according to claim 1, of the formula:

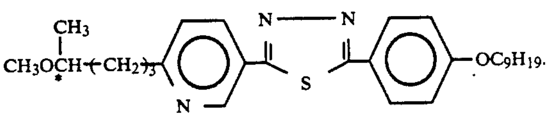

72. A compound according to claim 1, of the formula:

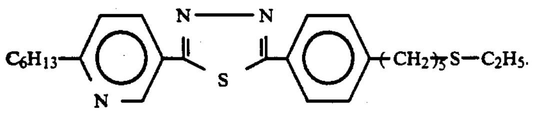

73. A compound according to claim 1, of the formula:

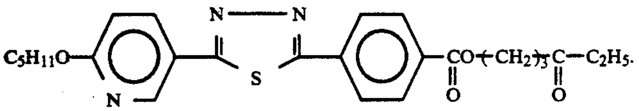

74. A compound according to claim 1, of the formula:

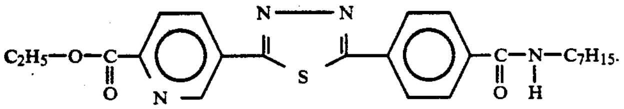

75. A compound according to claim 1, of the formula:

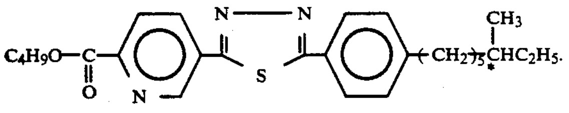

76. A compound according to claim 1, of the formula:

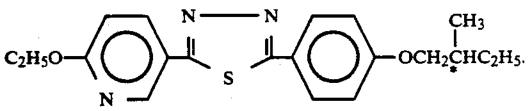

77. A compound according to claim 1, of the formula:

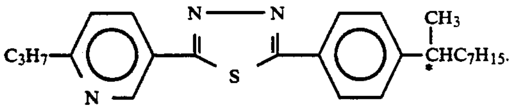

78. A compound according to claim 1, of the formula:

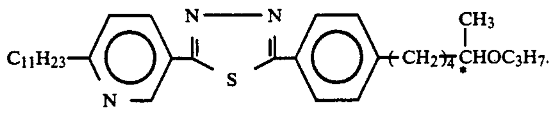

79. A compound according to claim 1, of the formula:

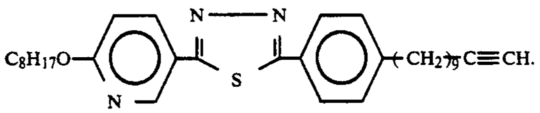

80. A compound according to claim 1, of the formula:

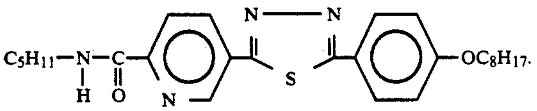

81. A compound according to claim 1, of the formula:

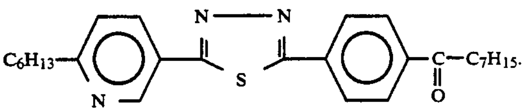

82. A compound according to claim 1, of the formula:

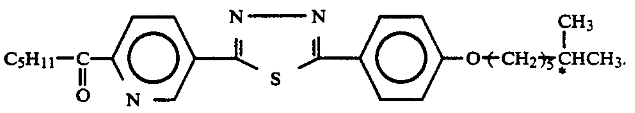

83. A compound according to claim 1, of the formula:

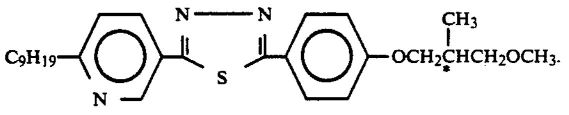

84. A compound according to claim 1, of the formula:

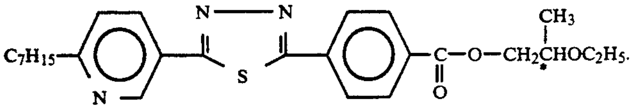

85. A compound according to claim 1, of the formula:

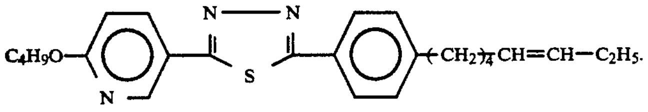

86. A compound according to claim 1, of the formula:

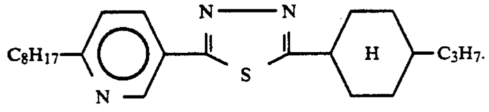

87. A compound according to claim 1, of the formula:

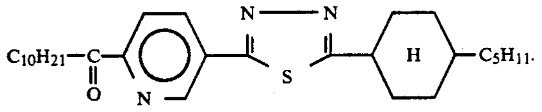

88. A compound according to claim 1, of the formula:

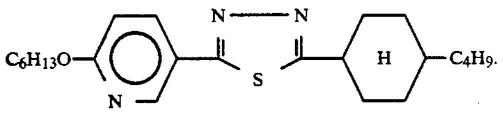

89. A compound according to claim 1, of the formula:

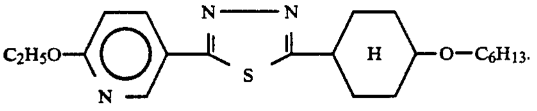

90. A compound according to claim 1, of the formula:

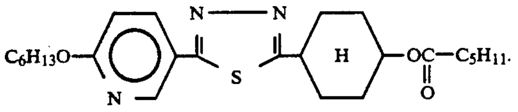

91. A compound according to claim 1, of the formula:

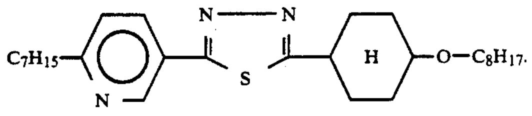

92. A compound according to claim 1, of the formula:

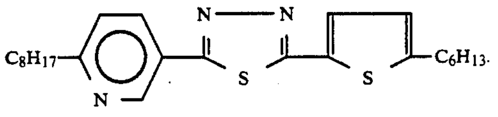

93. A compound according to claim 1, of the formula:

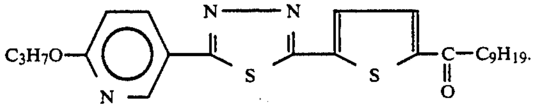

94. A compound according to claim 1, of the formula:

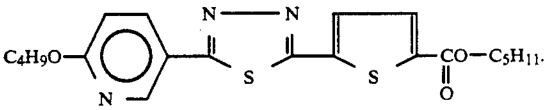

95. A compound according to claim 1, of the formula:

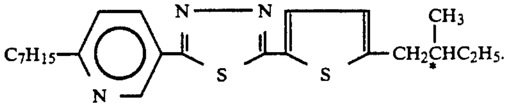

96. A compound according to claim 1, of the formula:

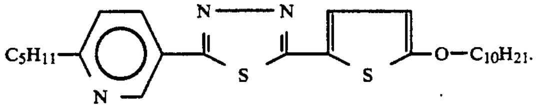

97. A compound according to claim 1, of the formula:

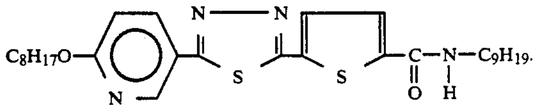

98. A compound according to claim 1, of the formula:

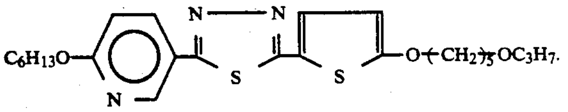

99. A compound according to claim 1, of the formula:

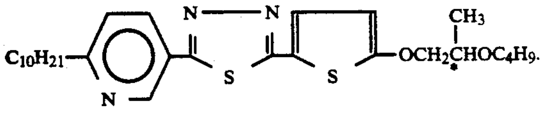

100. A compound according to claim 1, of the formula:

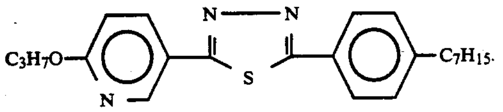

101. A compound according to claim 1, of the formula:

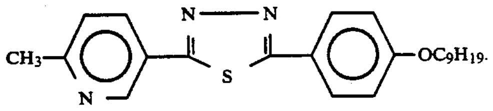

102. A compound according to claim 1, of the formula:

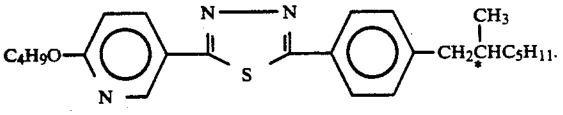

103. A compound according to claim 1, of the formula:

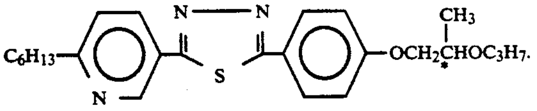

104. A compound according to claim 1, of the formula:

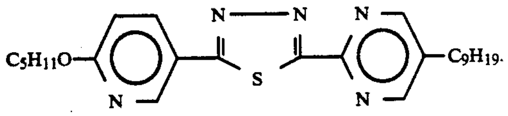

105. A compound according to claim 1, of the formula:

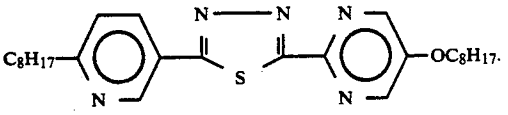

106. A compound according to claim 1, of the formula:

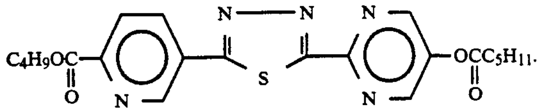

107. A compound according to claim 1, of the formula:

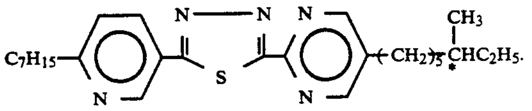

108. A compound according to claim 1, of the formula:

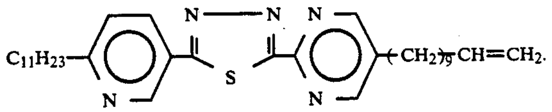

109. A compound according to claim 1, of the formula:

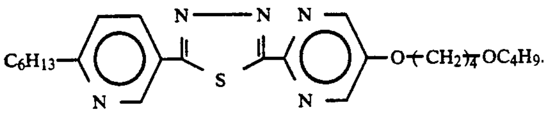

110. A compound according to claim 1, of the formula:

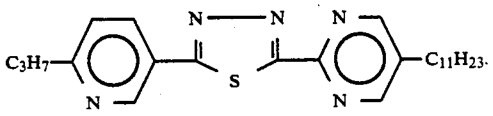

111. A compound according to claim 1, of the formula:

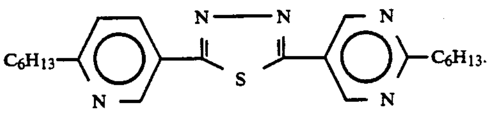

112. A compound according to claim 1, of the formula:

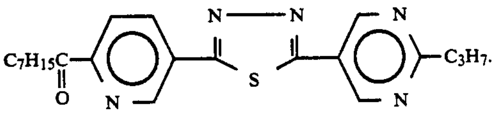

113. A compound according to claim 1, of the formula:

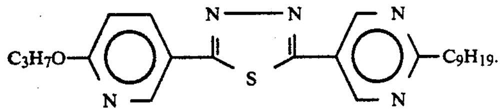

114. A compound according to claim 1, of the formula:

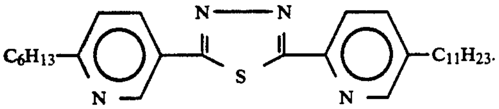

115. A compound according to claim 1, of the formula:

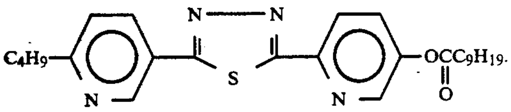

116. A compound according to claim 1, of the formula:

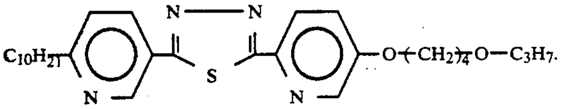

117. A compound according to claim 1, of the formula:

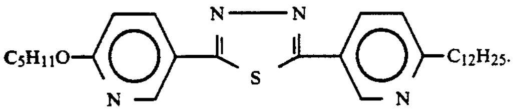

118. A compound according to claim 1, of the formula:

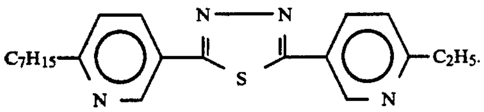

119. A compound according to claim 1, of the formula:

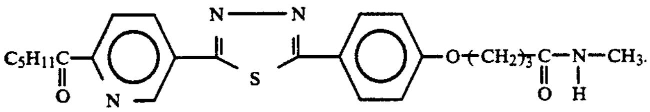

120. A compound according to claim 1, of the formula:

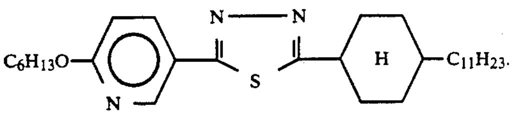

121. A compound according to claim 1, of the formula:

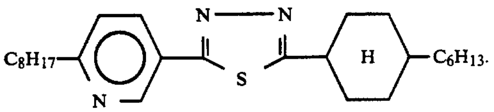

122. A compound according to claim 1, of the formula:

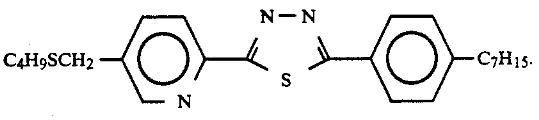

123. A compound according to claim 1, of the formula:

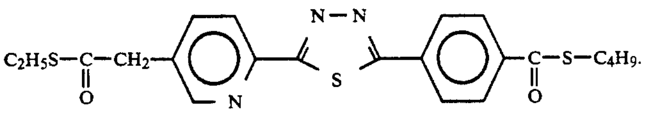

124. A compound according to claim 1, of the formula:

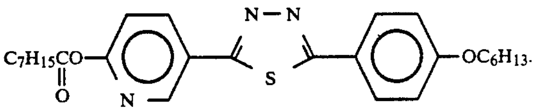

125. A compound according to claim 1, of the formula:

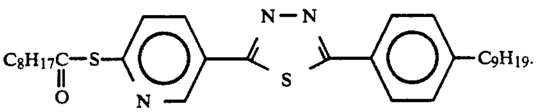

126. A compound according to claim 1, of the formula:

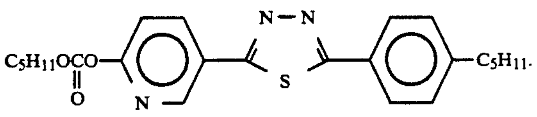

127. A compound according to claim 1, of the formula:

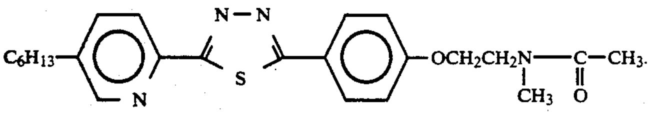

128. A compound according to claim 1, of the formula:

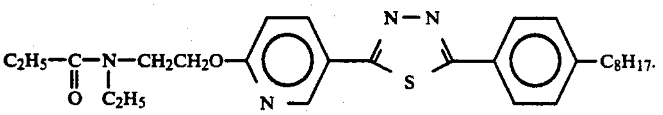

129. A liquid crystal composition comprising at least two mesomorphic compounds, at least one of which is a mesomorphic compound represented by the following formula:

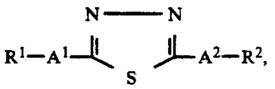
(I)

wherein $R^1$ and $R^2$ respectively denote a linear or branched alkyl group having 1-18 carbon atoms capable of including one or non-neighboring two or more methylene groups which can be replaced with at least one species of —Z—,

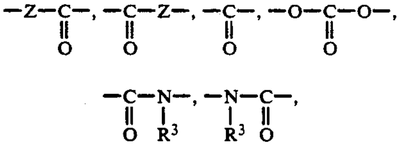

—CH═CH— and —C≡C—, wherein Z denotes —O— or —S— and $R^3$ denotes hydrogen or an alkyl group having 1-5 carbon atoms; $A^1$ denotes

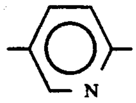
or
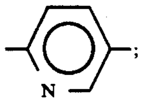
;

and $A^2$ denotes any one of

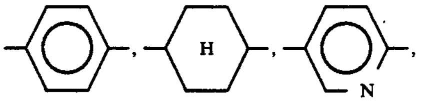

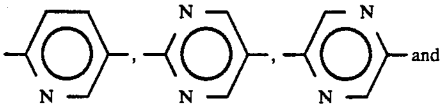
and

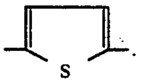
.

130. A liquid crystal device, comprising a pair of electrode plates and a liquid crystal composition according to claim 129 disposed between the electrode plates.

131. A liquid crystal composition according to claim 129, which has a chiral smectic phase.

132. A liquid crystal device according to claim 130, which further comprises an alignment control layer on the electrode plates.

133. A liquid crystal device according to claim 132, wherein the alignment control layer has been subjected to rubbing.

134. A liquid crystal device according to claim 131, wherein the pair of electrodes are disposed with a spacing therebetween sufficiently small to release the helical structure in the chiral smectic phase of the liquid crystal.

135. A liquid crystal composition according to claim 129, wherein said mesomorphic compound represented by the formula (I) is a compound according to any one of claims 2-128.

136. A liquid crystal device according to claim 130, wherein said mesomorphic compound represented by the formula (I) is a compound according to any one of claims 2-128.

* * * * *

UNITED STATES PATENT AND TRADEMARK OFFICE
CERTIFICATE OF CORRECTION

PATENT NO. : 5,076,961

DATED : December 31, 1991

INVENTOR(S) : SHINICHI NAKAMURA ET AL.

It is certified that error appears in the above-identified patent and that said Letters Patent is hereby corrected as shown below:

On the Title page, item [56], References Cited,

U.S. Patent Documents, insert
--4,367,924 1/83 Clark et al......350/334--.

Foreign Patent Documents, insert

| | | |
|---|---|---|
| --107216 | 8/81 | Japan |
| 193426 | 11/84 | Japan |
| 193427 | 11/84 | Japan |
| 156046 | 8/85 | Japan |
| 156047 | 8/85 | Japan |
| 245142 | 10/86 | Japan |
| 246722 | 11/86 | Japan |
| 246723 | 11/86 | Japan |
| 242724 | 11/86 | Japan |
| 249024 | 11/86 | Japan |
| 249025 | 11/86 | Japan |
| 051644 | 3/87 | Japan |
| 045258 | 2/88 | Japan |
| 222148 | 9/88 | Japan--. |

Other Publications, insert
--Appl. Phys. Lett., Vol. 18, No. 4 (Feb. 1971) 127:28.--.

"Herdegger," (both occurrences) should read --Hardegger,--.

COLUMN 51

(175), "$OC_6H_{11}$" should read --$OC_5H_{11}$--.

UNITED STATES PATENT AND TRADEMARK OFFICE

CERTIFICATE OF CORRECTION

PATENT NO. : 5,076,961

DATED : December 31, 1991

INVENTOR(S) : SHINICHI NAKAMURA ET AL. Page 2 of 2

It is certified that error appears in the above-identified patent and that said Letters Patent is hereby corrected as shown below:

COLUMN 68

Line 53, "N-(5-butyl-21-" should read --N-(5-butyl-2- --.

COLUMN 69

Line 9, "2-(5-butyl-21" should read --2-(5-butyl-2--.

COLUMN 71

Line 9, "mixed" should read --¶ The liquid crystal composition A was further mixed--.

COLUMN 90

Line 47, "—CH≡C—," should read ---C≡C—,--.

Signed and Sealed this

Twenty-ninth Day of June, 1993

Attest:

MICHAEL K. KIRK

Attesting Officer

*Acting Commissioner of Patents and Trademarks*